United States Patent [19]

Takano et al.

[11] Patent Number: 5,521,145
[45] Date of Patent: May 28, 1996

[54] IMINOTHIAZOLINE DERIVATIVES AND HERBICIDES CONTAINING THEM AS ACTIVE INGREDIENTS

[75] Inventors: Minoru Takano, Kameoka; Masayuki Enomoto, Takarazuka; Kazuo Saito, Toyonaka; Satoru Kizawa, Kakogawa, all of Japan

[73] Assignee: Sumitomo Chemical Company, Ltd., Osaka, Japan

[21] Appl. No.: 415,569

[22] Filed: Apr. 3, 1995

[30] Foreign Application Priority Data

Apr. 4, 1994 [JP] Japan .................... 6-065959

[51] Int. Cl.$^6$ ............... A01N 43/72; C07D 295/04
[52] U.S. Cl. ............... 504/225; 504/221; 504/235; 504/247; 504/266; 504/267; 504/270; 504/277; 544/52; 544/105; 544/354; 546/157; 546/158; 548/165; 548/169; 548/170; 548/171; 548/173; 548/190; 548/194; 548/198; 548/181
[58] Field of Search ................... 548/190, 194, 548/198, 181, 165, 169, 170, 171, 173; 504/266, 270, 277, 267, 247, 221, 225, 235; 546/157, 158; 544/52, 105, 354

[56] References Cited

FOREIGN PATENT DOCUMENTS

| | | | |
|---|---|---|---|
| 0318253 | 5/1989 | European Pat. Off. | 548/194 |
| 0420194 | 4/1991 | European Pat. Off. | 548/194 |
| 0446802 | 9/1991 | European Pat. Off. | 548/190 |
| 648772 | 5/1995 | European Pat. Off. | |
| 2531606 | 2/1977 | Germany | 548/190 |
| 1027561 | 1/1963 | United Kingdom | 548/190 |

OTHER PUBLICATIONS

CA 93:150177x Synthesis . . . thiazoles. Pathak et al., p. 712, 1980.
CA 95:132728q Synthesis . . . -fluoroarylthiazoles. Pathak et al., p. 659, 1981.
CA 114:62123y Sulfonylated . . . herbicides. Wolf et al., p. 694, 1991.
Chemical Abstracts, vol. 88, No. 9, 27 Feb. 1978 (abstract No. 62383b).
Patent Astracts of Japan, vol. 17, No. 617 (C–1129), 15 Nov. 1993.

*Primary Examiner*—Joseph K. McKane
*Attorney, Agent, or Firm*—Birch, Stewart, Kolasch & Birch

[57] ABSTRACT

There is disclosed an iminothiazoline derivative of the general formula:

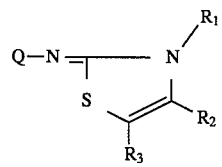

wherein $R_1$ is (halo)alkyl, (halo)alkenyl, (halo)alkynyl or the like; $R_2$ is (halo)alkyl, optionally substituted aryl, formyl, cyano or the like; $R_3$ is hydrogen, (halo)alkyl or the like; and Q is a group of the particular general formula. Also disclosed are a herbicide containing a herbicidally effective amount of the iminothiazoline derivative and a method for controlling unfavorable weeds, which includes applying a herbicidally effective amount of the iminothiazoline derivative to an area where the unfavorable weeds grow or will grow.

22 Claims, No Drawings

IMINOTHIAZOLINE DERIVATIVES AND HERBICIDES CONTAINING THEM AS ACTIVE INGREDIENTS

FIELD OF THE INVENTION

The present invention relates to novel iminothiazoline derivatives and herbicides containing them as active ingredients.

SUMMARY OF THE INVENTION

The present inventors have intensively studied to develop effective herbicides. As a result, they have found that particular iminothiazoline derivatives have excellent herbicidal activity, thereby completing the present invention.

Thus, the present invention provides an iminothiazoline derivative (hereinafter referred to as the present compound) of the general formula:

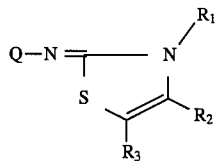  [1]

wherein $R_1$ is $C_1$-$C_6$ (halo)alkyl, $C_3$-$C_6$ (halo)alkenyl, $C_3$-$C_6$ (halo)alkynyl, $C_3$-$C_7$ (halo)cycloalkyl, $C_3$-$C_7$ cycloalkyl $C_1$-$C_3$ alkyl, cyano $C_1$-$C_3$ alkyl or $C_1$-$C_5$ (halo)alkoxy $C_1$-$C_5$ (halo)alkyl;

$R_2$ is $C_1$-$C_6$ (halo)alkyl, $C_3$-$C_7$ (halo)cycloalkyl, $C_7$-$C_{17}$ aralkyl which may be substituted with one or more $C_1$-$C_3$ (halo)alkyl groups, $C_1$-$C_3$ (halo)alkoxy groups or halogen atoms, aryl which may be substituted with one or more $C_1$-$C_3$ (halo)alkyl groups, $C_1$-$C_3$ (halo)alkoxy groups or halogen atoms, formyl, cyano or a group of the general formula: $CO_2R_7$ or $CONR_8R_9$;

$R_3$ is hydrogen, $C_1$-$C_6$ (halo)alkyl or a group of the general formula: $CO_2R_6$;

Q is a group of the general formula:

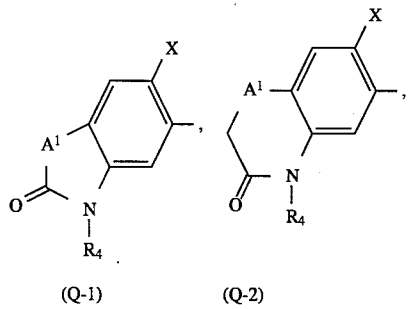

X is hydrogen, chlorine or fluorine;
Y is chlorine, fluorine, bromine, nitro or cyano;
$A^1$ is oxygen, sulfur, —$CH_2$ or —NH;

$A^2$ is oxygen or sulfur;
$R_4$ is $C_1$-$C_6$ (halo)alkyl, $C_3$-$C_6$ (halo)alkenyl, $C_3$-$C_6$ (halo)alkynyl, $C_3$-$C_7$ (halo)cycloalkyl, cyano $C_1$-$C_3$ alkyl, $C_1$-$C_3$ (halo)alkoxy C1-$C_3$ (halo)alkyl, ($C_1$-$C_6$ (halo)alkyl)carbonyl, ($C_1$-$C_6$ alkoxy)carbonyl, hydrogen or a group of the general formula:

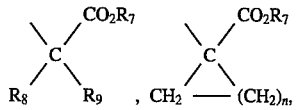

(P-1)   (P-2)

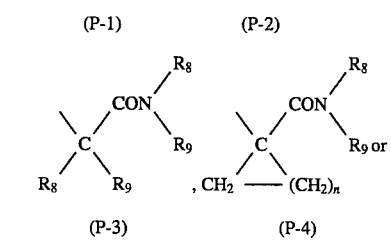

(P-3)   (P-4)

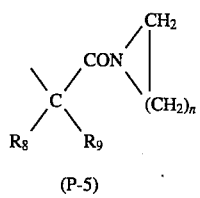

(P-5)

$R_5$ is hydrogen, $C_1$-$C_6$ (halo)alkyl or a group of the general formula: $CH_2OR_4$ or $CO_2R_7$;

$R_6$ is hydrogen or $C_1$-$C_3$ (halo)alkyl;

B is nitro, cyano, $SO_2Cl$, tetrahydrophthalimide group or a group of the general formula: $CO_2R_7$, $CR_6$=$NOR_4$, $CH$=$C(R_6)CO_2R_7$, $CHX^1CHX^2CO_2R_7$, $SR_4$, $OR_4$, $NHR_4$, $NHSO_2R_{10}$, $COR_6$ or $SO_2OR_4$;

$X^1$ and $X^2$ are the same or different and are independently hydrogen, chlorine or bromine;

$R_7$ is hydrogen, $C_1$-$C_{10}$ (halo)alkyl, $C_3$-$C_7$ (halo)cycloalkyl, $C_3$-$C_7$ cycloalkenyl, $C_3$-$C_6$ (halo)alkenyl, $C_3$-$C_6$ (halo)alkynyl, cyano $C_1$-$C_3$ alkyl, $C_1$-$C_3$ alkoxy $C_1$-$C_3$ alkyl, ($C_1$-$C_5$ (halo)alkoxy)carbonyl $C_1$-$C_3$ alkyl, aryl which may be substituted with one or more $C_1$-$C_3$ (halo)alkyl groups, $C_1$-$C_3$ (halo)alkoxy groups or halogen atoms, benzyl or a group of the general formula: N=$CR_6R_6$, $NR_6R_6$ or

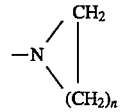

$R_8$ and $R_9$ are the same or different and are independently hydrogen, $C_1$-$C_6$ (halo)alkyl, $C_3$-$C_6$ (halo)alkenyl or $C_3$-$C_6$ (halo)alkynyl;

$R_{10}$ is $C_1$-$C_6$ (halo)alkyl, $C_3$-$C_8$ (halo)cycloalkyl or aryl which may be substituted with one or more $C_1$-$C_3$ (halo)alkyl groups, $C_1$-$C_3$ (halo)alkoxy groups or halogen atoms;

n is an integer of 1 to 5; and the term "(halo)" as used in the names of the above substituents means that they may be substituted with one or more halogen atoms.

The present invention further provides a herbicide containing the above iminothiazoline derivative as an active ingredient.

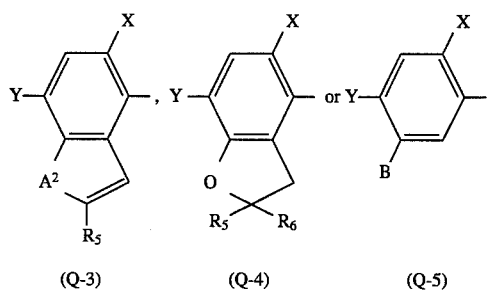

DETAILED DESCRIPTION OF THE INVENTION

The present compounds may have optical isomers based on the configuration of an asymmetric carbon atom, and it should be recognized that these optical isomers and mixtures thereof are included within the scope of the present invention.

The present compounds are represented by the general formula [1] wherein the substituents $R_1$, $R_2$, $R_3$ and Q are defined as follows:

The substituent $R_1$ is $C_1$–$C_6$ (halo)alkyl, $C_3$–$C_6$ (halo)alkenyl, $C_3$–$C_6$ (halo)alkynyl, $C_3$–$C_7$ (halo)cycloalkyl, $C_3$–$C_7$ cycloalkyl $C_1$–$C_3$ alkyl, cyano $C_1$–$C_3$ alkyl or $C_1$–$C_5$ (halo)alkoxy $C_1$–$C_5$ (halo)alkyl.

Examples of the $C_1$–$C_6$ (halo)alkyl group are methyl, ethyl, n-propyl, isopropyl, sec-butyl, difluoromethyl, 2-fluoroethyl and 3-fluoropropyl.

Examples of the $C_3$–$C_6$ (halo)alkenyl group are allyl, 2-chloro-2-propenyl and 1- methyl-2-propenyl.

Examples of the $C_3$–$C_6$ (halo)alkynyl group are propargyl and 3-iodo-2-propynyl.

Examples of the $C_3$–$C_7$ (halo)cycloalkyl group are cyclopropyl, cyclopentyl and cyclohexyl.

Examples of the $C_3$–$C_7$ cycloalkyl $C_1$–$C_3$ alkyl group are cyclopropylmethyl.

Examples of the cyano $C_1$–$C_3$ alkyl group are cyanomethyl and 2-cyanoethyl.

Examples of the $C_1$–$C_5$ (halo)alkoxy $C_1$–$C_5$ (halo)alkyl group are methoxymethyl.

The substituent $R_2$ is $C_1$–$C_6$ (halo)alkyl, $C_3$–$C_7$ (halo)cycloalkyl, $C_7$–$C_{17}$ aralkyl which may be substituted with one or more $C_1$–$C_3$ (halo)alkyl groups, $C_1$–$C_3$ (halo)alkoxy groups or halogen atoms, aryl which may be substituted with one or more $C_1$–$C_3$ (halo)alkyl groups, $C_1$–$C_3$ (halo)alkoxy groups or halogen atoms, formyl, cyano or a group of the general formula: $CO_2R_7$ or $CONR_8R_9$.

Examples of the $C_1$–$C_6$ (halo)alkyl group are methyl, ethyl, isopropyl, tertbutyl, trifluoromethyl, chlorodifluoromethyl, difluoromethyl, pentafluoroethyl, fluoromethyl, chloromethyl, bromomethyl, 2-chloro-1,1-dimethylethyl, 2-bromo-1,1-dimethylethyl and 1,1,2,2-tetrafluoroethyl.

Examples of the $C_3$–$C_7$ (halo)cycloalkyl group are cyclopropyl, 2-chlorocyclopropyl, cyclopentyl and cyclohexyl.

Examples of the $C_7$–$C_{17}$ aralkyl group are benzyl, α-methylbenzyl and α,α-dimethylbenzyl. The $C_7$–$C_{17}$ aralkyl group may be substituted with one or more $C_1$–$C_3$ (halo)alkyl groups, $C_1$–$C_3$ (halo)alkoxy groups or halogen atoms, examples of which are chlorine, bromine, fluorine, methyl, trifluoromethyl and trifluoromethoxy.

Examples of the aryl group are phenyl, α-naphthyl and β-naphthyl. The aryl group may be substituted with one or more $C_1$–$C_3$ (halo)alkyl groups, $C_1$–$C_3$ (halo)alkoxy groups or halogen atoms, examples of which are chlorine, bromine, fluorine, methyl, trifluoromethyl and trifluoromethoxy. Specific examples of the aryl group are 4-chlorophenyl, 4-fluorophenyl, 4-bromophenyl, 4-methylphenyl, 4-trifluoromethoxyphenyl, 2-chlorophenyl, 2-fluorophenyl, 2-bromophenyl, 2-methylphenyl, 2-methoxyphenyl, 2,4-difluorophenyl, 4-trifluoromethylphenyl, 2-fluoro-4-trifluoromethylphenyl, 3-chlorophenyl, 3-bromophenyl, 3-fluorophenyl, 3-trifluoromethylphenyl and 3-trifluoromethoxyphenyl.

Examples of the group of the general formula: $CO_2R_7$ are carboxyl, methoxycarbonyl and ethoxycarbonyl.

Examples of the group of the general formula: $CONR_8R_9$ are carbamoyl, N-methylcarbamoyl and N,N-dimethylcarbamoyl.

The substituent $R_3$ is hydrogen, $C_1$–$C_6$ (halo)alkyl or a group of the general formula: $CO_2R_6$.

Examples of the $C_1$–$C_6$ (halo)alkyl group are methyl.

Examples of the group of the general formula: $CO_2R_6$ are ethoxycarbonyl and methoxycarbonyl.

The substituent $R_4$ is $C_1$–$C_6$ (halo)alkyl, C3-$C_6$ (halo)alkenyl, $C_3$–$C_6$ (halo)alkynyl, $C_3$–$C_7$ (halo)cycloalkyl, cyano $C_1$–$C_3$ alkyl, $C_1$–$C_3$ (halo)alkoxy $C_1$–$C_3$ (halo)alkyl, ($C_1$–$C_6$ (halo)alkyl)carbonyl, ($C_1$–$C_6$ alkoxy)carbonyl, hydrogen or a group of the general formula:

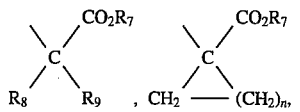

(P-1)        (P-2)

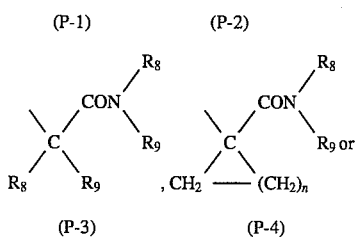

(P-3)        (P-4)

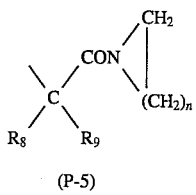

(P-5)

Examples of the $C_1$–$C_6$ (halo)alkyl group are methyl, ethyl, n-propyl, isopropyl, n-butyl, sec-butyl, isobutyl, n-amyl, isoamyl, 2-fluoroethyl, 2,2-difluoroethyl and 3-fluoropropyl.

Examples of the $C_3$–$C_6$ (halo)alkenyl group are allyl, 2-chloro-2-propenyl, 1-methyl-2-propenyl, 3-butenyl, 2-butenyl, 3,3-dichloro-2-propenyl, 3-methyl-2-butenyl and 2-methyl-3-butenyl.

Examples of the $C_3$–$C_6$ (halo)alkynyl group are propargyl, 1-methyl-2-propynyl, 2-butynyl, 1,1-dimethyl-2-propynyl and 3-iodo-2-propynyl.

Examples of the $C_3$–$C_7$ (halo)cycloalkyl group are cyclopropyl, cyclopentyl and cyclohexyl.

Examples of the cyano $C_1$–$C_3$ alkyl group are cyanomethyl, 1-cyanoethyl and 2-cyanoethyl.

Examples of the $C_1$–$C_3$ (halo)alkoxy $C_1$–$C_3$ (halo)alkyl group are methoxymethyl, ethoxymethyl, isopropyloxymethyl and 1-methoxyethyl.

Examples of the ($C_1$–$C_6$ (halo)alkyl)carbonyl group are acetyl, propanoyl, trifluoroacetyl, chloroacetyl, 2-methylpropanoyl and dichloroacetyl.

Examples of the ($C_1$–$C_6$ alkoxy)carbonyl group are methoxycarbonyl and ethoxycarbonyl.

Examples of the group of the general formula (P-1) are 1-(methoxycarbonyl)ethyl, 1-(ethoxycarbonyl)ethyl, 1-(cyclopentyloxycarbonyl)ethyl, 1-(dimethylaminooxycarbonyl)ethyl, 1-(isopropylidenaminooxycarbonyl)ethyl, methoxycarbonylmethyl, isopropoxycarbonylmethyl, cyclopentyloxycarbonylmethyl and 2-fluoroethoxycarbonylmethyl.

Examples of the group of the general formula (P-2) are 1-(methoxycarbonyl)cyclopropyl, 1-(ethoxycarbonyl)cyclopropyl, 1-(isopropoxycarbonyl)cyclopropyl, 1-(isopropylidenaminooxycarbonyl)cyclopropyl and 1-(diethylaminooxycarbonyl)cyclopropyl.

Examples of the group of the general formula (P-3) are 1-(dimethylcarbamoyl)ethyl, 1-(diethylcarbamoyl)ethyl, 1-(methylcarbamoyl)ethyl, 1-(2,2,2-trifluoroethylcarbamoyl)ethyl, diethylcarbamoylmethyl, allylcarbamoylmethyl and bis(2,2,2-trifluoroethyl)carbamoylmethyl.

Examples of the group of the general formula (P-4) are 1-(dimethylcarbamoyl)cyclopropyl, 1-(diethylcarbamoyl)cyclopropyl, 1-(isopropylcarbamoyl)cyclopropyl, 1-(2,2,2-trifluoroethylcarbamoyl )cyclopropyl and 1 -(propargylcarbamoyl)cyclopropyl.

Examples of the group of the general formula (P-5) are 1-(pyrolidin-1-ylcarbonyl)ethyl, 1-(aziridin-1-ylcarbonyl)ethyl, pyrolidin-1-ylcarbonylmethyl and piperidinocarbonylmethyl.

The substituent $R_5$ is hydrogen, $C_1-C_6$ (halo)alkyl or a group of the general formula: $CH_2OR_4$ or $CO_2R_7$.

Examples of the group of the general formula: $CH_2OR_4$ are acetoxymethyl, trifluoroacetyloxymethyl, chloroacetyloxymethyl, methoxymethoxymethyl and hydroxymethyl.

Examples of the group of the general formula: $CO_2R_7$ are methoxycarbonyl, ethoxycarbonyl, 2,2,2-trifluoroethoxycarbonyl, isopropoxycarbonyl, cyclopentyloxycarbonyl, allyloxycarbonyl, propargyloxycarbonyl and 2-methoxyethoxycarbonyl.

Examples of the $C_1-C_6$ (halo)alkyl group are methyl, ethyl, isopropyl, dibromomethyl and bromomethyl.

The substituent $R_6$ is hydrogen or $C_1-C_3$ (halo)alkyl.

Example of the $C_1-C_3$ (halo)alkyl group are methyl, ethyl, isopropyl, dibromomethyl and bromomethyl.

The substituent $R_7$ is hydrogen, $C_1-C_{10}$ (halo)alkyl, $C_3-C_7$ (halo)cycloalkyl, $C_3-C_7$ cycloalkenyl, $C_3-C_6$ (halo)alkenyl, $C_3-C_6$ (halo)alkynyl, cyano $C_1-C_3$ alkyl, $C_1-C_3$ alkoxy $C_1-C_3$ alkyl, $(C_1-C_5$ (halo)alkoxy)carbonyl $C_1-C_3$ alkyl, aryl which may be substituted with one or more $C_1-C_3$ (halo)alkyl groups, $C_1-C_3$ (halo)alkoxy groups or halogen atoms, benzyl, or a group of the general formula: $N=CR_6R_6$, $NR_6R_6$ or

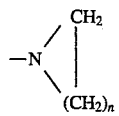

Examples of the $C_1-C_{10}$ (halo)alkyl group are methyl, ethyl, n-propyl, isopropyl, n-butyl, sec-butyl, tert-butyl, n-amyl, isoamyl, tert-amyl, 2,2,2-trifluoroethyl, 2,2-difluoroethyl, 2-fluoroethyl, 3-fluoropropyl, 2-chloroethyl, 3-chloropropyl, 2,3-dichloropropyl, 2-fluoro- 1-(fluoromethyl)ethyl, 10-chlorodecyl, 8-chlorooctyl, 2-bromoethyl, 2-chloro-1-methylethyl, 7-bromoheptyl and 8-bromooctyl.

Examples of the $C_3-C_7$ (halo)cycloalkyl group are cyclopropyl, cyclopentyl, cyclohexyl, 4-fluorocyclohexyl, 3,3,4,4-tetrafluorocyclopentyl, 2,2-difluorocyclopropyl and 2,2-dichlorocyclopropyl.

Examples of the $C_3-C_7$ cycloalkenyl group are 2-cyclopentenyl, 3-cyclopentenyl, 2-cyclohexenyl and 3-cyclohexenyl.

Examples of the $C_3-C_6$ (halo)alkenyl group are allyl, 2-chloro-2-propenyl, 1-methyl-2-propenyl, 3-butenyl, 2-butenyl, 3,3-dichloro-2-propenyl, 3-methyl-2-butenyl and 2-methyl-3-butenyl.

Examples of the $C_3-C_6$ (halo)alkynyl group are propargyl, 1-methyl-2-propynyl, 2-butynyl, 1,1-dimethyl-2-propynyl, 3-butynyl and 3-iodo-2-propynyl.

Examples of the cyano $C_1-C_3$ alkyl group are cyanomethyl, 1-cyanoethyl and 2-cyanoethyl.

Examples of the $C_1-C_3$ alkoxy $C_1-C_3$ alkyl group are methoxymethyl, ethoxymethyl, propoxymethyl, isopropyloxymethyl, 1-methoxyethyl, 2-methoxyethyl and 3-methoxypropyl.

Examples of the $(C_1-C_5$ (halo)alkoxy)carbonyl $C_1-C_3$ alkyl group are methoxycarbonylmethyl, ethoxycarbonylmethyl, n-butyloxycarbonylmethyl, 2-(ethoxycarbonyl)ethyl, 1-(methoxycarbonyl)ethyl, 1-(ethoxycarbonyl)ethyl, 1-(propoxycarbonyl)ethyl and 1-(2-chloroethyloxycarbonyl)ethyl.

Examples of the group of the general formula: $N=CR_6R_6$ are isopropylidenamino, 1-ethylpropylidenamino and perfluoroisopropylidenamino.

Examples of the group of the general formula: $NR_6R_6$ are dimethylamino, diethylamino and bis(2,2,2-trifluoroethyl)amino.

Examples of the aryl group are phenyl, α-naphthyl and β-naphthyl. The aryl group may be substituted with one or more $C_1-C_3$ (halo)alkyl groups, $C_1-C_3$ (halo)alkoxy groups or halogen atoms, examples of which are chlorine, bromine, fluorine, methyl, trifluoromethyl and trifluoromethoxy. Specific examples of the aryl group are 4-methylphenyl, 3-methylphenyl, 4-chloro-phenyl, 3-chlorophenyl, 4-trifluoromethoxyphenyl, 3-fluorophenyl, 4-fluorophenyl, 2-fluorophenyl and 3-trifluoromethoxyphenyl.

Examples of the group of the general formula:

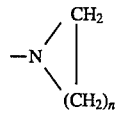

are 1-aziridinyl, 1-pyrrolidinyl and 1-piperidinyl.

The substituents $R_8$ and $R_9$ are the same or different and are independently hydrogen, $C_1-C_6$ (halo)alkyl, $C_3-C_6$ (halo)alkenyl or $C3-C_6$ (halo)alkynyl.

Examples of the $C_1-C_6$ (halo)alkyl group are methyl, ethyl, n-propyl, isopropyl, sec-butyl, difluoromethyl, 2-fluoroethyl and 3-fluoropropyl.

Examples of the $C_3-C_6$ (halo)alkenyl group are allyl, 2-chloro-2-propenyl and 1-methyl-2-propynyl.

Examples of the $C_3-C_6$ (halo)alkynyl group are propargyl and 3-iodo-2propynyl.

The substituent $R_{10}$ is $C_1-C_6$ (halo)alkyl, $C_3-C_8$ (halo)cycloalkyl, or aryl which may be substituted with one or more $C_1-C_3$ (halo)alkyl groups, $C_1-C_3$ (halo)alkoxy groups or halogen atoms.

Examples of the $C_1-C_6$ (halo)alkyl group are methyl, ethyl, n-propyl, i-propyl, n-butyl, trifluoromethyl, 2,2,2-trifluoroethyl, chloromethyl, bromomethyl, 2-chloroethyl and 3-chloropropyl.

Examples of the $C_3-C_8$ (halo)cycloalkyl group are cyclopropyl, 2-chlorocyclopropyl, cyclopentyl, cyclohexyl and cycloheptyl.

Examples of the aryl group are phenyl, α-naphthyl and β-naphthyl. The aryl group may be substituted with one or more $C_1-C_3$ (halo)alkyl groups, $C_1-C_3$ (halo)alkoxy groups or halogen atoms, examples of which are chlorine, bromine, fluorine, methyl, trifluoromethyl and trifluoromethoxy.

The substituent B is nitro, cyano, $SO_2Cl$, tetrahydrophthalimide group or a group of the general formula:

CO$_2$R$_7$, CR$_6$=NOR$_4$, CH=C(R$_6$)CO$_2$R$_7$, CHX$^1$CHX$^2$—CO$_2$R$_7$, SR$_4$, OR$_4$, NHR$_4$, NHSO$_2$R$_{10}$, COR$_6$ or SO$_2$OR$_4$.

Examples of the group of the general formula: CO$_2$R$_7$ are methoxycarbonyl, ethoxycarbonyl, isopropoxycarbonyl, cyclopentyloxycarbonyl, 2,2,2-trifluoroethoxycarbonyl, 2-chloroethoxycarbonyl, allyloxycarbonyl, propargyloxycarbonyl, 2-methoxyethoxycarbonyl and 2-isopropoxyethoxycarbonyl.

Examples of the group of the general formula: CR$_6$=NOR$_4$ are methoxyiminomethyl, propargyloxyiminomethyl, methoxycarbonylmethoxyiminomethyl, 1-(methoxycarbonyl)ethoxyiminomethyl, cyclopentyloxyiminomethyl, 1-(methoxyimino)ethyl, 1-(propargyloxyimino)ethyl, 1-(methoxycarbonylmethoxyimino)ethyl, 1-[1-(methoxycarbonyl)ethoxyimino]ethyl and 1-(cyclopentyloxyimino)ethyl.

Examples of the group of the general formula: CH=C(R$_6$)CO$_2$R$_7$ are 2-(methoxycarbonyl)ethenyl, 2-(ethoxycarbonyl)ethenyl, 2-(isopropoxycarbonyl)ethenyl, 2-(cyclopentyloxycarbonyl)ethenyl, 2-(2-fluoroethoxycarbonyl)ethenyl, 2-(2-methoxyethoxycarbonyl)ethenyl, 2-(methoxycarbonyl)-1-propenyl, 2-(ethoxycarbonyl)-1-propenyl, 2-(isopropoxycarbonyl)-1-propenyl, 2-(cyclopentyloxycarbonyl)-1-propenyl, 2-(2-fluoroethoxycarbonyl)-1-propenyl and 2-(2-methoxyethoxycarbonyl)-1-propenyl.

Examples of the group of the general formula: CHX$^1$CHX$^2$CO$_2$R$_7$ are 2-chloro-2-methoxycarbonylethyl, 2-chloro-2-ethoxycarbonylethyl, 2-chloro-2-n-pentoxycarbonylethyl, 2-chloro-2-cyclopentyloxycarbonylethyl, 2-chloro-2-(2-fluoroethoxycarbonyl)ethyl and 2-chloro-2-(2-methoxyethoxycarbonyl)ethyl.

Examples of the group of the general formula: SR$_4$ are 1-(methoxycarbonyl)ethylthio, methoxycarbonylmethylthio, cyclopentyloxycarbonylmethylthio, 2-methoxyethoxycarbonylmethylthio, methylthio, isopropylthio, propargylthio, 1-methylpropargylthio, allylthio, cyclopentylthio, 2-fluoroethylthio, 2,2,2-trifluoroethylthio, 1-(n-pentyloxycarbonyl)ethylthio, acetylthio, trifluoroacetylthio and methoxycarbonylthio.

Examples of the group of the general formula: OR$_4$ are 1-(methoxycarbonyl)ethoxy, methoxycarbonylmethoxy, cyclopentyloxycarbonylmethoxy, 2-methoxyethoxycarbonylmethoxy, methoxy, isopropoxy, propargyloxy, 1-methylpropargyloxy, allyloxy, cyclopentyloxy, 2-fluoroethoxy, 2,2,2-trifluoroethoxy, 1-(n-pentyloxycarbonyl)ethoxy, acetoxy, trifluoroacetyloxy and methoxycarbonyloxy.

Examples of the group of the general formula: NHR$_4$ are 1-(methoxycarbonyl)ethylamino, methoxycarbonylmethylamino, cyclopentyloxycarbonylmethylamino, 2-methoxyethoxycarbonylmethylamino, methylamino, isopropylamino, propargylamino, 1-methylpropargylamino, allylamino, cyclopentylamino, 2-fluoroethylamino, 2,2,2-trifluoroethylamino, 1-(n-pentyloxycarbonyl)ethylamino, acetylamino, trifluoroacetylamino and methoxycarbonylamino.

Examples of the group of the general formula: NHSO$_2$R$_{10}$ are methylsulfonylamino, ethylsulfonylamino, n-propylsulfonylamino, n-butylsulfonylamino, n-amylsulfonylamino, i-propylsulfonylamino, chloromethylsulfonylamino, 2-chloroethylsulfonylamino, 3-chloropropylsulfonylamino, 4-chlorobutylsulfonylamino, trifluoromethylsulfonylamino and 2,2,2-trifluoroethylsulfonylamino.

Examples of the group of the general formula: COR$_6$ are acetyl, ethylcarbonyl, formyl, 2,2,2-trifluoroethylcarbonyl and chloroacetyl.

Examples of the group of the general formula: SO$_2$OR$_4$ are methoxysulfonyl, ethoxysulfonyl, cyclopentyloxysulfonyl and propargyloxysulfonyl.

Examples of the group represented by Q are:

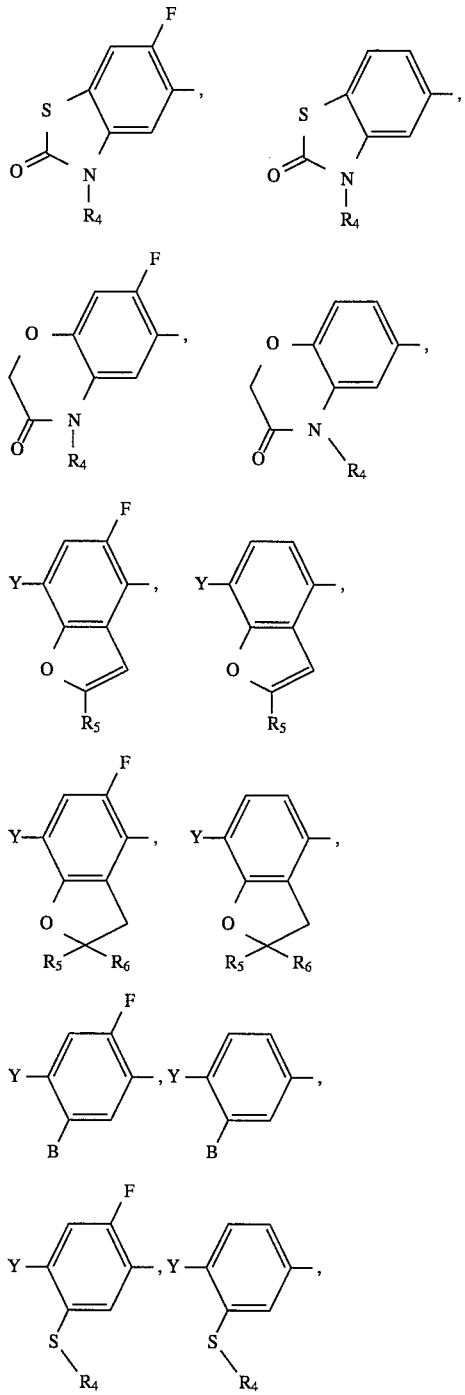

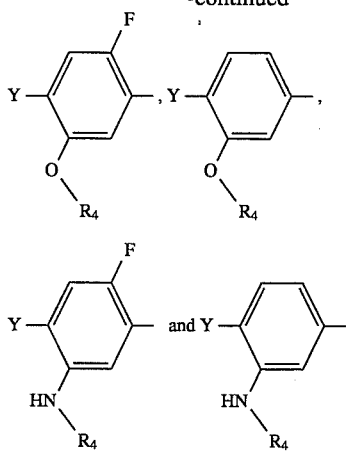

In the present compound, the substituents preferred in view of their herbicidal activity are as follows:

For the substituent $R_1$, $C_1$–$C_6$ (halo)alkyl is preferred, and $C_1$–$C_3$ alkyl such as methyl is particularly preferred.

For the substituent $R_2$, halogen-substituted $C_1$–$C_6$ alkyl, cyano or a group of the general formula: $CO_2R_7$ or $CONR_8R_9$ is preferred, and halogen-substituted $C_1$–$C_3$ alkyl such as trifluoromethyl, chlorodifluoromethyl, difluoromethyl or pentafluoroethyl is particularly preferred.

For the substituent $R_3$, hydrogen or a group of the general formula: $CO2R_6$ is preferred, and hydrogen is particularly preferred.

For the substituent Q, a group of the general formula: (Q-1), (Q-2) or (Q-5) is preferred.

Preferred examples of the present compound are those where $R_1$ is methyl, $R_2$ is trifluoromethyl, $R_3$ is hydrogen, Q is a group of the general formula (Q-5), X is fluorine, Y is chlorine and B is methoxycarbonylmethylthio; those where $R_1$ is methyl, $R_2$ is chlorodifluoromethyl, $R_3$ is hydrogen, Q is a group of the general formula (Q-1), X is fluorine, $A^1$ is sulfur and $R_4$ is sec-butyl; and those where $R_1$ is methyl, $R_2$ is trifluoromethyl, $R_3$ is hydrogen, Q is a group of the general formula (Q-2), X is fluorine, $A^1$ is oxygen and $R_4$ is propargyl.

The present compounds can be produced by the following production processes:

Production Process A

The present compounds can be produced by reacting a thiourea derivative of the general formula:

Q—NHC(=S)NH—$R_1$   (2)

wherein Q and $R_1$ are each as defined above, with a ketone derivative of the general formula:

$D^1CH(R_3)C(=O)R_2$   (3)

wherein $R_2$ and $R_3$ are each as defined above and $D^1$ is chlorine, bromine or iodine.

This reaction is usually effected in a solvent. The reaction temperature is usually in the range of 0° to 200° C., and the reaction time is usually in the range of a moment to 48 hours. The compound [3] is usually used at an amount of 1 to 5 moles per mole of the compound [2].

Examples of the solvent to be used are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and diethylene glycol dimethyl ether; ketones such as acetone, methyl ethyl ketone, methyl isobutyl ketone, isophorone and cyclohexanone; alcohols such as methanol, ethanol, isopropanol, t-butanol, octanol, cyclohexanol, methyl cellosolve, diethylene glycol and glycerol; esters such as ethyl formate, ethyl acetate, butyl acetate and diethyl carbonate; nitro compounds such as nitromethane and nitrobenzene; nitriles such as acetonitrile and isobutyronitrile; acid amides such as formamide, N,N-dimethylformamide and acetamide; sulfur compounds such as dimethylsulfoxide and sulforane; water; or mixture thereof.

In this reaction, a base may be used, if necessary, at a catalytic amount to an excess amount per mole of the compound [2]. Examples of the base are sodium acetate.

After completion of the reaction, the reaction mixture is poured into water, to which saturated aqueous sodium bicarbonate solution is added, and the mixture is subjected to ordinary post-treatments such as extraction with an organic solvent and concentration or evaporation of the reaction solvent. If necessary, the product may be purified by a technique such as chromatography or recrystallization. Thus, the desired present compound can be obtained.

Production Process B

The present compounds can also be obtained by reacting the compound [2] with the compound [3] to give a compound of the general formula:

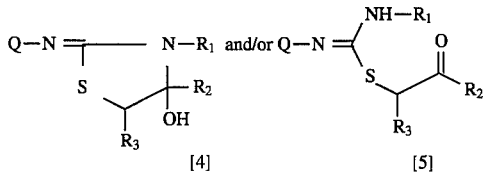

wherein $R_1$, $R_2$, $R_3$ and Q are each as defined above (hereinafter referred to as the reaction 1), and then dehydrating the compounds [4] and/or [5] (hereinafter referred to as the reaction 2).

The reaction 1 is usually effected in a solvent. The reaction temperature is usually in the range of 0° to 150° C., and the reaction time is usually in the range of a moment to 24 hours. The compound [3] is usually used at an amount of 1 to 5 moles per mole of the compound [2].

Examples of the solvent to be used are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and ethylene glycol dimethyl ether; ketones such as acetone, methyl ethyl ketone, methyl isobutyl ketone, isophorone and cyclohexanone; alcohols such as methanol, ethanol, isopropanol, t-butanol, octanol, cyclohexanol, methyl cellosolve, diethylene glycol and glycerol; esters such as ethyl formate, ethyl acetate, butyl acetate and diethyl carbonate; nitro compounds such as nitromethane and nitrobenzene; nitriles such as acetonitrile and isobutyronitrile; acid amides such as formamide, N,N-dimethylfonmamide and acetamide; sulfur compounds such as dimethylsulfoxide and sulforane; water; or mixture thereof.

In the reaction 1, a dehydrohalogenating agent may be used, if necessary, at a catalytic amount to an excess amount per mole of the compound [2]. Examples of the dehydrohalogenating agent are organic bases such as pyridine, triethylamine, N,N-diethylaniline, sodium acetate and sodium formate; and inorganic bases such as sodium hydroxide, potassium hydroxide, sodium carbonate and potassium carbonate.

After completion of the reaction, the reaction mixture is poured into water, if necessary, and the mixture is subjected to ordinary post-treatments such as extraction with an organic solvent and concentration. The compounds [4] and/ or [5] may be used in isolated or non-isolated form for the reaction 2.

The reaction 2 is usually effected in the presence of an acid without any solvent or in an solvent. The reaction temperature is usually in the range of 0° to 200° C., and the reaction time is usually a moment to 48 hours. The acid is usually used at a catalytic amount to an excess amount, e.g., 0.001 to 100 moles, per mole of the compound [2].

Examples of the solvent to be used are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and diethylene glycol dimethyl ether; nitro compounds such as nitroethane and nitrobenzene; nitriles such as acetonitrile and isobutyronitrile; acid amides such as formamide, N,N-dimethylformamide and acetamide; sulfur compounds such as dimethylsulfoxide and sulforane; or mixture thereof. The following acids can also be used as the solvent.

Examples of the acid to be used are sulfonic acids such as p-toluenesulfonic acid, methanesulfonic acid and trifluoromethanesulfonic acid; and mineral acids such as sulfuric acid and hydrochloric acid.

After completion of the reaction, the reaction mixture is poured into water, if necessary, and the mixture is subjected to ordinary post-treatments such as extraction with an organic solvent and concentration. If necessary, the product may be purified by a technique such as chromatography or recrystallization. Thus, the desired present compound can be obtained.

Production Process C

The present compounds of the general formula:

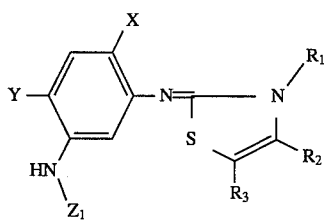

[1-1]

wherein $Z^1$ is $R_4$ or $SO_2R_{10}$ and X, Y, $R_1$, $R_2$, $R_3$, $R_4$ and $R_{10}$ are each as defined above, which can also be produced by the following production route C:

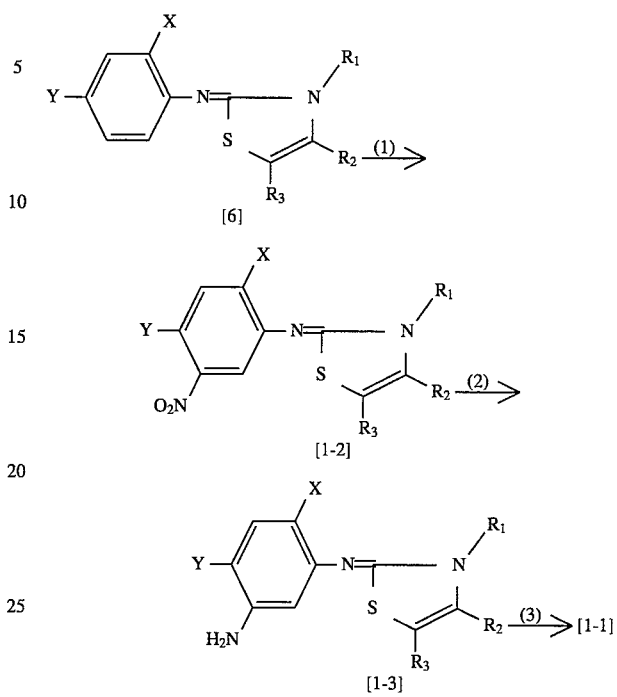

The reaction steps (1), (2) and (3) of the production route C will be explained below.

(1) The compound [1–2] can be produced by nitrating the compound [6] with a nitrating agent such as nitric acid in a solvent such as inorganic acids such as sulfuric acid; organic acids such as acetic acid; halogenated hydrocarbons, e.g., chloroform, dichloroethylene; or mixtures of these solvents with water.

(2) The compound [1–3] can be produced by reducing the compound [1–2] with metal powder such as iron powder or tin powder in a solvent such as organic acids, e.g., acetic acid; inorganic acids such as hydrochloric acid; halogenated hydrocarbons, e.g., chloroform, dichloroethylene; esters, e.g., ethyl acetate; alcohols, e.g., methanol, ethanol; or mixtures of these solvents with water, or by reducing the compound [1–2] under hydrogen atmosphere with a catalyst such as palladium-carbon and platinum-carbon in a solvent such as esters, e.g., ethyl acetate, diethyl carbonate; ethers, e.g., tetrahydrofuran, 1,4-dioxane; alcohols, e.g., methanol, ethanol; or mixtures thereof.

(3) The compound [1–1] wherein $Z^1$ is a group of the general formula: $SO_2R_{10}$ can be produced by reacting the compound [1–3] with a compound of the general formula:

$$D^1\text{—}SO_2R_{10} \qquad (7)$$

wherein $D^1$ and $R_{10}$ are each as defined above, in the presence of a base such as organic bases, e.g., pyridine, triethylamine; or inorganic bases, e.g., sodium hydroxide, potassium carbonate, sodium hydride, in a solvent such as organic bases, e.g., pyridine; halogenated hydrocarbons, e.g., chloroform, dichloroethane, chlorobenzene; nitro compounds, e.g., nitromethane, nitroethane; acid amides, e.g., N,N-dimethylformamide; or sulfur compounds, e.g., dimethylsulfoxide, sulforane.

The compound [1—1] wherein $Z^1$ is other than hydrogen or the group of the general formula: $SO_2R_{10}$ can be produced by heating the compound [1–3] with a compound of the general formula:

$$D^2\text{—}Z^1 \tag{8}$$

wherein $D^2$ is chlorine, bromine, iodine, $C_1$–$C_4$ alkylsulfonyloxy (e.g., methanesulfonyloxy), optionally substituted benzenesulfonyloxy (e.g., p-toluenesulfonyloxy optionally substituted with one or more $C_1$–$C_4$ alkyl groups, $C_1$–$C_4$ alkoxy groups or halogen atoms, benzenesulfonyloxy optionally substituted with one or more $C_1$–$C_4$ alkyl groups, $C_1$–$C_4$ alkoxy groups or halogen atoms), in the absence of any solvent or in the presence of a solvent and a base as described above for dehydrohalogenation.

The compound [1—1] wherein $Z^1$ is ($C_1$–$C_3$ (halo)alkyl)carbonyl can be produced by reacting the compound [1–3] with an acid anhydride corresponding to the compound of the general formula: $D_2$-$Z^1$ in a solvent such as organic acids, e.g., acetic acid.

Production Process D

The compound [1–3] can also be produced by the following production route D:

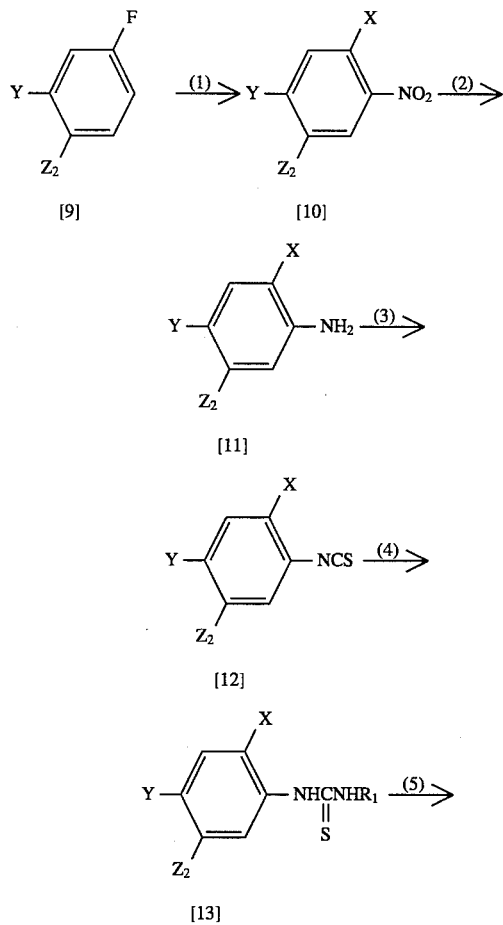

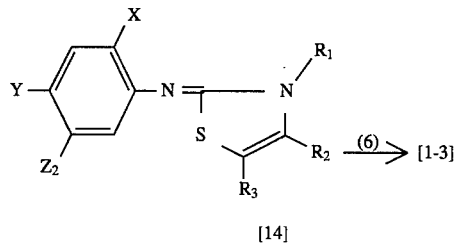

wherein $Z^2$ is a cyclic imide group (e.g., tetrahydrophthalimide group, maleimide group), and X, Y, $R_1$, $R_2$ and $R_3$ are each as defined above.

The reaction steps (1), (2), (3), (4), (5) and (6) of the production route D will be explained below.

(1) The compound [10] can be produced by nitrating the compound [9] with a nitrating agent such as nitric acid in a solvent such as inorganic acids, e.g., sulfufic acid; organic acids such as acetic acid; halogenated hydrocarbons, e.g., chloroform, dichloroethane; or mixtures of these solvents with water.

(2) The compound [11] can be produced by reducing the compound [10] with metal powder such as iron powder or tin powder in a solvent such as organic acids, e.g., acetic acid; inorganic acids such as hydrochloric acid; halogenated hydrocarbons, e.g., chloroform, dichloroethylene; esters, e.g., ethyl acetate; alcohols, e.g., methanol, ethanol; or mixtures of these solvents with water, or by reducing the compound [10] under hydrogen atmosphere with a catalyst such as palladium-carbon and platinum-carbon in a solvent such as esters, e.g., ethyl acetate, diethyl carbonate; ethers, e.g., tetrahydrofuran, 1,4-dioxane; alcohols, e.g., methanol, ethanol; or mixtures thereof.

(3) The compound [12] can be produced by reacting the compound [11] with phosgene or by reacting the compound [11] with carbon disulfide in the presence of a base to give the corresponding dithiocarbamate which is then reacted with a haloformate such as methyl chloroformate.

(4) The compound [13] can be produced by reacting the compound [12] with a compound of the general formula:

$$R_1\text{—}NH_2 \tag{15}$$

wherein $R_1$ is as defined above.

This reaction is usually effected in a solvent. The reaction temperature is usually in the range of 0° to 200° C., and the reaction time is usually a moment to 48 hours. The compound [15] is usually used at an amount of 1 to 3 moles per mole of the compound [12].

Examples of the solvent to be used are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and diethylene glycol dimethyl ether; esters such as ethyl formate, ethyl acetate, butyl acetate and diethyl carbonate; nitro compounds such as nitroethane and nitrobenzene; nitriles such as acetonitrile and isobutyronitrile; tertiary amines such as pyridine, triethylamine, N,N-diethylaniline, tributylamine and N-methylmorphorine; acid amides such as formamide, N,N-dimethylformamide and acetamide; sulfur compounds such as dimethylsulfoxide and sulforane; water; or mixture thereof.

In this reaction, there is usually no need to use a base, but a base may be used in some cases. Examples of the base to be used are organic bases such as pyridine, triethylamine and N,N-diethylaniline; and inorganic bases such as sodium hydroxide, potassium hydroxide, sodium carbonate, potassium carbonate and sodium hydride.

(5) The compound [14] can be produced by reacting the compound [13] with the compound [3] thorough the process according to the production process A or B.

(6) The compound [1–3] can be produced by dissolving the compound [14] in an alcohol solvent such as methanol or ethanol, and then adding thereto an aqueous solution containing an inorganic base such as sodium hydroxide or potassium hydroxide at an amount of 1.0 equivalent to large excess, followed by heating, if necessary, for hydrolysis, or using 1.0 equivalent to large excess of hydrous hydrazine for hydrolysis.

Production Process E

The present compound of the general formula:

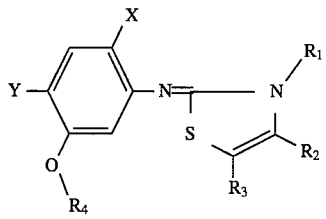

[1-4]

wherein X, Y, $R_1$, $R_2$, $R_3$ and $R_4$ are each as defined above, can also be produced by the following production route E.

Production Route E

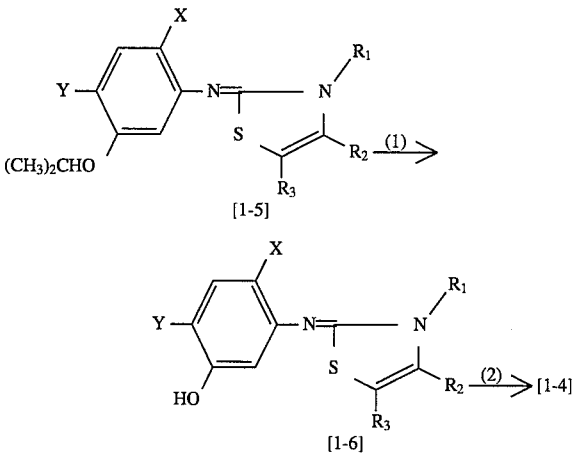

The reaction steps (1) and (2) of the production route E will be explained below.

(1) The compound [1–6] can be produced by subjecting the compound [1–5] to deisopropylation with an inorganic acid such as sulfuric acid or hydrochloric acid; a Lewis acid such as aluminum chloride; or a solution of hydrogen bromide and acetic acid.

(2) The compound [1–4] can be produced by reacting the compound [1–6] with a compound of the general formula:

$$D^1—R_4 \qquad (16)$$

wherein $D^1$ and $R_4$ are each as defined above, in a solvent such as aromatic hydrocarbons, e.g., benzene, toluene; halogenated hydrocarbons, e.g., chloroform, dichloroethane, chlorobenzene; ethers, e.g., tetrahydrofuran, dioxane; ketones, e.g., acetone, methyl isobutyl ketone; nitro compounds, e.g., nitromethane, nitroethane; acid amides, e.g., N,N-dimethylformamide; sulfur compounds, e.g., dimethylsulfoxide, sulforane; water; or mixtures thereof, in the presence of a base such as inorganic bases, e.g., sodium hydroxide, potassium carbonate, sodium hydride; or organic bases, e.g., pyfidine, triethylamine.

Production Process F

The present compound wherein the substituent B is a group containing an ester residue (e.g., $CO_2R_{77}$, $CH{=}C(R_6)CO_2R_{77}$, $CHX^1CHX^2CO_2R_7$, wherein $R_{77}$ is a substituent having the same definition as that of $R_7$ exclusive of hydrogen; those which are defined by the general formulae in the definition of the substituent B wherein $R_4$ is a group of the general formula (P-1) or (P-2)) can be produced by subjecting the present compound having any other ester residue than the ester residue of the desired present compound to ester exchange reaction using an alcohol corresponding to the ester residue of the desired present compound as a solvent by the addition of an organic acid such as p-toluenesulfonic acid or an inorganic acid such as concentrated sulfuric acid.

Production Process G

The present compound wherein the substituent B is a group having an ester residue can be produced by convening the present compound wherein a carboxyl group is substituted for the ester residue into the corresponding acid chloride with a chlorinating agent such as thionyl chloride or phosgene, and then reacting the acid chloride with an alcohol corresponding to the ester residue in the presence of a base such as pyridine or triethylamine, if necessary.

Production Process H

The present compound wherein the substituent $R_2$ is carboxyl can be produced by acting the present compound wherein the substituent $R_2$ is a group of the general formula: $CO_2R_{77}$ wherein $R_{77}$ is as defined above, with an aqueous solution containing an inorganic base such as sodium hydroxide or potassium hydroxide in a solvent such as ethers, e.g., dioxane, tetrahydrofuran; alcohols, e.g., methanol, ethanol; water; or n-fixtures thereof.

Production Process I

The present compound wherein the substituent $R_2$ is a group of the general formula: $CONR_8R_9$ wherein $R_8$ and $R_9$ are each as defined above, can be produced by marking the present compound wherein the substituent $R_2$ is carboxyl with a compound of the general formula:

$$HNR_8R_9 \qquad (17)$$

wherein $R_8$ and $R_9$ are each as defined above, in an ether solvent such as diethyl ether or tetrahydrofuran in the presence of a dehydration-condensing agent such as carbodiimidazole, or by convening the present compound wherein the substituent $R_2$ is carboxyl into the corresponding acid chloride with a chlorinating agent such as thionyl chloride, phosgene or phosphorous oxychloride, and then reacting the acid chloride with the compound [17] in a solvent such as ethers, e.g., diethyl ether, tetrahydrofuran; or alcohols, e.g., isopropanol.

Production Process J

The present compound wherein the substituent $R_2$ is cyano can be produced by dehydrating the present compound wherein the substituent $R_2$ is carbamoyl with an agent such as phosgene, phosphorous oxychloride, thionyl chloride, carbodiimidazole or dicyclohexylcarbodiimide (DCC).

Production Process K

The present compound wherein the substituent B is a group of the general formula: $CR_6=NOH$ wherein $R_6$ is as defined above can be produced by reacting the present compound wherein the substituent B is a group of the general formula: $COR_6$ with hydroxyamine hydrochloride in an alcohol solvent such as methanol, ethanol or isopropanol in the presence of a base such as organic bases such as triethylamine or pyridine; or inorganic bases such as potassium carbonate or sodium carbonate, if necessary.

Production Process L

The present compound wherein the substituent B is a group of the general formula: $CR_6=NOR_{44}$ wherein $R_{44}$ is a substituent having the same definition as that of $R_4$ exclusive of hydrogen, and $R_6$ is as defined above, can be produced by reacting the present compound wherein the substituent B is a group of the general formula: $CR_6=NOH$ wherein $R_6$ is as defined above with a compound of the general formula:

$$D^1-R_{44} \qquad (18)$$

wherein $R_{44}$ and $D^1$ are each as defined above, in a solvent such as aromatic hydrocarbons, e.g., benzene, toluene; halogenated hydrocarbons, e.g., chloroform, dichloroethane, chlorobenzene; ethers, e.g., tetrahydrofuran, dioxane; ketones, e.g., acetone, methyl isobutyl ketone; nitro compounds, e.g., nitromethane, nitroethane; acid amides, e.g., N,N-dimethylformamide; sulfur compounds, e.g., dimethylsulfoxide, sulforane; water; or mixtures thereof, in the presence of a base such as inorganic bases, e.g., sodium hydroxide, potassium carbonate, sodium hydride; or organic bases, e.g., pyridine, triethylamine.

Some examples of the present compound are shown by the respective compound numbers in Tables 1 to 5.

TABLE 1

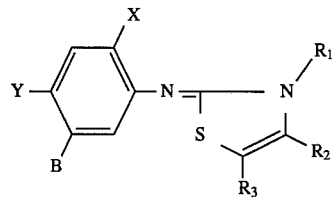

| Compound No. | X | Y | $R_1$ | $R_2$ | $R_3$ | B |
|---|---|---|---|---|---|---|
| 101 | F | Cl | $CH_3$ | $CH_3$ | H | $OCH(CH_3)C\equiv CH$ |
| 102 | F | Cl | $CH_3$ | $CH_3$ | H | $SCH_2COOCH_3$ |
| 103 | F | Cl | $CH_3$ | $CF_3$ | H | $OCH(CH_3)C\equiv CH$ |
| 104 | F | Cl | $CH_3$ | $CF_3$ | H | $SCH_2COOCH_3$ |
| 105 | F | Cl | $CH_3$ | $C_4H_9(tert)$ | H | $SCH_2COOCH_3$ |
| 106 | F | Cl | $CH_3$ | $CH_3$ | H | $OC_3H_7(iso)$ |
| 107 | F | Cl | $CH_3$ | $C_4H_9(tert)$ | H | $OC_3H_7(iso)$ |
| 108 | F | Cl | $CH_3$ | $CF_3$ | H | $OC_3H_7(iso)$ |
| 109 | F | Cl | $CH_3$ | $CF_3$ | H | OH |
| 110 | F | Cl | $CH_3$ | $CF_3$ | H | $OCH(CH_3)COOC_2H_5$ |
| 111 | F | Cl | $CH_3$ | $CF_3$ | H | $OCH_2COOCH_3$ |
| 112 | F | Cl | $CH_3$ | $CF_3$ | H | $OCH_2C(Cl)=CH_2$ |
| 113 | F | Cl | $CH_3$ | $CF_3$ | H | $OCH_2CH=CH_2$ |
| 114 | F | Cl | $CH_3$ | $CF_3$ | H | $O-CH_2CN$ |
| 115 | F | Cl | $CH_3$ | $CF_3$ | H | $OCH_2C\equiv CH$ |
| 116 | F | Cl | $CH_3$ | $CF_3$ | H | $SCH(CH_3)COOCH_3$ |
| 117 | F | Cl | $CH_3$ | $CF_3$ | H | COOH |
| 118 | F | Cl | $CH_3$ | $CF_3$ | H | $COOCH_3$ |
| 119 | F | Cl | $CH_3$ | $CF_3$ | H | $COOC_3H_7(iso)$ |
| 120 | F | Cl | $CH_3$ | $CF_3$ | H | CHO |
| 121 | F | Cl | $CH_3$ | $CF_3$ | H | $CH=CHCOOCH_3$ |
| 122 | F | Cl | $CH_3$ | $CF_3$ | H | $NO_2$ |
| 123 | F | Cl | $CH_3$ | $CF_3$ | H | $SCH_2COOC_2H_5$ |
| 124 | F | Cl | $CH_3$ | $CF_3$ | H | $SCH_2COOC_3H_7(iso)$ |
| 125 | F | Cl | $CH_3$ | $CF_3$ | H | $SCH_2COOC_5H_{11}(n)$ |
| 126 | F | Cl | $CH_3$ | $CF_3$ | H | $SCH_2COOC_3H_5(c)$ |
| 127 | F | Cl | $CH_3$ | $CF_3$ | H | $SCH(CH_3)COOC_2H_5$ |
| 128 | F | Cl | $CH_3$ | $CF_3$ | H | $SCH(CH_3)COOC_3H_7(iso)$ |
| 129 | F | Cl | $CH_3$ | $CF_3$ | H | $SCH(CH_3)COOC_5H_{11}(n)$ |
| 130 | F | Cl | $CH_3$ | $CF_3$ | H | $SCH(CH_3)COOC_5H_9(c)$ |

TABLE 1-continued

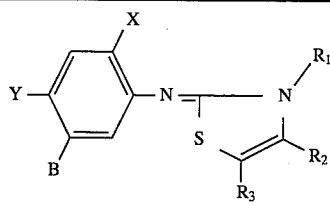

| Compound No. | X | Y | $R_1$ | $R_2$ | $R_3$ | B |
|---|---|---|---|---|---|---|
| 131 | F | Cl | $CH_3$ | $CF_3$ | H | $OCH_3$ |
| 132 | F | Cl | $CH_3$ | $CF_3$ | H | $OC_2H_5$ |
| 133 | F | Cl | $CH_3$ | $CF_3$ | H | $OCH(CH_3)C_3H_7(n)$ |
| 134 | F | Cl | $CH_3$ | $CF_3$ | H | $OCF_2CF_2H$ |
| 135 | F | Cl | $CH_3$ | $CF_3$ | H | $OCH_2COOC_2H_5$ |
| 136 | F | Cl | $CH_3$ | $CF_3$ | H | $OCH_2COOC_3H_7(n)$ |
| 137 | F | Cl | $CH_3$ | $CF_3$ | H | $OCH_2COOC_4H_9(n)$ |
| 138 | F | Cl | $CH_3$ | $CF_3$ | H | $OCH_2COOC_5H_{11}(n)$ |
| 139 | F | Cl | $CH_3$ | $CF_3$ | H | $OCH_2COOC_3H_7(iso)$ |
| 140 | F | Cl | $CH_3$ | $CF_3$ | H | $OCH_2COOC_5H_9(c)$ |
| 141 | F | Cl | $CH_3$ | $CF_3$ | H | $OC_5H_9(c)$ |
| 142 | F | Cl | $CH_3$ | $CF_3$ | H | $NHCH_2COOCH_3$ |
| 143 | F | Cl | $CH_3$ | $CF_3$ | H | $NHCH_2COOC_2H_5$ |
| 144 | F | Cl | $CH_3$ | $CF_3$ | H | $NHCH_2COOC_3H_7(iso)$ |
| 145 | F | Cl | $CH_3$ | $CF_3$ | H | $NHCH(CH_3)COOCH_3$ |
| 146 | F | Cl | $CH_3$ | $CF_3$ | H | $NHCH(CH_3)COOC_2H_5$ |
| 147 | F | Cl | $CH_3$ | $CF_3$ | H | $NHSO_2CH_3$ |
| 148 | F | Cl | $CH_3$ | $CF_3$ | H | $NHSO_2C_2H_5$ |
| 149 | F | Cl | $CH_3$ | $CF_3$ | H | $NHSO_2CH_2CF_3$ |
| 150 | F | Cl | $CH_3$ | $CF_3$ | H | $NHSO_2CH_2Cl$ |
| 151 | F | Cl | $CH_3$ | $CF_3$ | H | $NHSO_2CH_2CH_2CH_2Cl$ |
| 152 | F | Cl | $CH_3$ | $CF_3$ | H | $SO_2OCH_3$ |
| 153 | F | Cl | $C_2H_5$ | $CF_3$ | H | $OC_3H_7(iso)$ |
| 154 | F | Cl | $C_3H_7(n)$ | $CF_3$ | H | $OC_3H_7(iso)$ |
| 155 | F | Br | $CH_3$ | $CF_3$ | H | $OC_3H_7(iso)$ |
| 156 | F | F | $CH_3$ | $CF_3$ | H | $OC_3H_7(iso)$ |
| 157 | H | Cl | $CH_3$ | $CF_3$ | H | $OCH_3$ |
| 158 | H | Cl | $CH_3$ | $CF_3$ | H | $OC_3H_7(iso)$ |
| 159 | H | Cl | $CH_3$ | $CF_3$ | H | $OCH_2CH=CH_2$ |
| 160 | H | Cl | $CH_3$ | $CF_3$ | H | $OCH_2C\equiv CH$ |
| 161 | H | Cl | $CH_3$ | $CF_3$ | H | $OCH(CH_3)C\equiv CH$ |
| 162 | H | Cl | $CH_3$ | $CF_3$ | H | $OCH_2C(Cl)=CH_2$ |
| 163 | H | Cl | $CH_3$ | $CF_3$ | H | $OCH_2CN$ |
| 164 | H | Cl | $CH_3$ | $CF_3$ | H | $SCH_2COOCH_3$ |
| 165 | H | Cl | $CH_3$ | $CF_3$ | H | $SCH_2COOC_2H_5$ |
| 166 | H | Cl | $CH_3$ | $CF_3$ | H | $SCH_2COOC_3H_7(iso)$ |
| 167 | H | Cl | $CH_3$ | $CF_3$ | H | $SCH_2COOC_5H_{11}(n)$ |
| 168 | H | Cl | $CH_3$ | $CF_3$ | H | $SCH_2COOC_5H_9(c)$ |
| 169 | H | Cl | $CH_3$ | $CF_3$ | H | $SCH(CH_3)COOCH_3$ |
| 170 | H | Cl | $CH_3$ | $CF_3$ | H | $SCH(CH_3)COOC_2H_5$ |
| 171 | H | Cl | $CH_3$ | $CF_3$ | H | $SCH(CH_3)COOC_3H_7(iso)$ |
| 172 | H | Cl | $CH_3$ | $CF_3$ | H | $SCH(CH_3)COOC_5H_{11}(n)$ |
| 173 | H | Cl | $CH_3$ | $CF_3$ | H | $SCH(CH_3)COOC_5H_9(c)$ |
| 174 | H | Cl | $CH_3$ | $CF_3$ | H | $OCH_2COOCH_3$ |
| 175 | H | Cl | $CH_3$ | $CF_3$ | H | $OCH_2COOC_2H_5$ |
| 176 | H | Cl | $CH_3$ | $CF_3$ | H | $OCH_2COOC_3H_7(n)$ |
| 177 | H | Cl | $CH_3$ | $CF_3$ | H | $OCH_2COOC_4H_9(n)$ |
| 178 | H | Cl | $CH_3$ | $CF_3$ | H | $OCH_2COOC_5H_{11}(n)$ |
| 179 | H | Cl | $CH_3$ | $CF_3$ | H | $OCH_2COOC_3H_7(iso)$ |
| 180 | H | Cl | $CH_3$ | $CF_3$ | H | $OCH_2COOC_5H_9(c)$ |
| 181 | H | Cl | $CH_3$ | $CF_3$ | H | $OCH(CH_3)COOCH_3$ |
| 182 | H | Cl | $CH_3$ | $CF_3$ | H | $OCH(CH_3)COOC_2H_5$ |
| 183 | H | Cl | $CH_3$ | $CF_3$ | H | $OCH(CH_3)COOC_3H_7(iso)$ |
| 184 | H | Cl | $CH_3$ | $CF_3$ | H | $OCH(CH_3)COOC_5H_{11}(n)$ |
| 185 | H | Cl | $CH_3$ | $CF_3$ | H | $OCH(CH_3)COOC_5H_9(c)$ |
| 186 | H | Cl | $CH_3$ | $CF_3$ | H | $OC_5H_9(c)$ |
| 187 | H | Cl | $CH_3$ | $CF_3$ | H | $NHCH_2COOCH_3$ |
| 188 | H | Cl | $CH_3$ | $CF_3$ | H | $NHCH_2COOC_2H_5$ |
| 189 | H | Cl | $CH_3$ | $CF_3$ | H | $NHCH_2COOC_3H_7(iso)$ |
| 190 | H | Cl | $CH_3$ | $CF_3$ | H | $NHCH(CH_3)COOCH_3$ |
| 191 | H | Cl | $CH_3$ | $CF_3$ | H | $NHCH(CH_3)COOC_2H_5$ |
| 192 | H | Cl | $CH_3$ | $CF_3$ | H | $NHSO_2CH_3$ |
| 193 | H | Cl | $CH_3$ | $CF_3$ | H | $NHSO_2C_2H_5$ |
| 194 | H | Cl | $CH_3$ | $CF_3$ | H | $NHSO_2CH_2Cl$ |

TABLE 1-continued

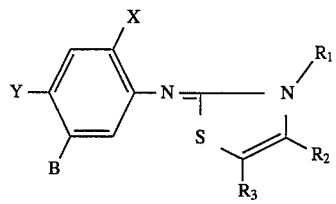

| Compound No. | X | Y | R₁ | R₂ | R₃ | B |
|---|---|---|---|---|---|---|
| 195 | H | Cl | CH₃ | CF₃ | H | NHSO₂CH₂CH₂CH₂Cl |
| 196 | F | Cl | CH₃ | CF₂Cl | H | OCH₂CO₂CH₃ |
| 197 | F | Cl | CH₃ | CF₂Cl | H | OCH₂CO₂C₂H₅ |
| 198 | F | Cl | CH₃ | CF₂Cl | H | OCH₂CO₂C₃H₇(iso) |
| 199 | F | Cl | CH₃ | CF₂Cl | H | OCH(CH₃)CO₂CH₃ |
| 200 | F | Cl | CH₃ | CF₂Cl | H | OCH(CH₃)CO₂C₂H₅ |
| 201 | F | Cl | CH₃ | CF₂Cl | H | OCH(CH₃)CO₂C₃H₇ |
| 202 | F | Cl | CH₃ | CF₂Cl | H | OCH(CH₃)CO₂C₃H₇(iso) |
| 203 | F | Cl | CH₃ | CF₂Cl | H | OCH(CH₃)CO₂C₅H₉(c) |
| 204 | F | Cl | CH₃ | CF₂Cl | H | OCH₃ |
| 205 | F | Cl | CH₃ | CF₂Cl | H | OC₃H₇(iso) |
| 206 | F | Cl | CH₃ | CF₂Cl | H | O—CH₂C≡CH |
| 207 | F | Cl | CH₃ | CF₂Cl | H | OCH(CH₃)C≡CH |
| 208 | F | Cl | CH₃ | CF₂Cl | H | O—CH₂CH=CH₂ |
| 209 | F | Cl | CH₃ | CF₂Cl | H | SCH₂CO₂CH₃ |
| 210 | F | Cl | CH₃ | CF₂Cl | H | SCH₂CO₂C₅H₉(c) |
| 211 | F | Cl | CH₃ | CF₃ | H | NH₂ |
| 212 | F | Cl | CH₃ | CF₃ | H | NHCOCH₃ |
| 213 | F | Cl | CH₃ | CF₃ | H | NHCOCH₂Cl |
| 214 | F | Cl | CH₃ | CF₃ | H | NHCOCF₃ |
| 215 | F | Cl | CH₃ | CF₃ | H | NHCH₂C≡CH |
| 216 | F | Cl | CH₃ | CF₃ | H | NHCH₂CH=CH₂ |
| 217 | F | Cl | CH₃ | CN | H | OCH₂C≡CH |
| 218 | F | Cl | CH₃ | CN | H | OCH(CH₃)C≡CH |
| 219 | F | Cl | CH₃ | CN | H | OCH₂CH=CH₂ |
| 220 | F | Cl | CH₃ | CN | H | OC₃H₇(iso) |
| 221 | F | Cl | CH₃ | CN | H | SCH₂CO₂CH₃ |
| 222 | F | Cl | CH₃ | CF₃ | H | CO₂C₃H₇(n) |
| 223 | F | Cl | CH₃ | CF₃ | H | CO₂C₂H₅ |
| 224 | F | Cl | CH₃ | CF₃ | H | CO₂C₅H₉(c) |
| 225 | F | Cl | CH₃ | CF₃ | H | CO₂C₆H₁₁(c) |
| 226 | F | Cl | CH₃ | CF₃ | H | CO₂CH₂CH₂Cl |
| 227 | F | Cl | CH₃ | CF₃ | H | CO₂CH₂CH=CHCl |
| 228 | F | Cl | CH₃ | CF₃ | H | COCH₃ |
| 229 | F | Cl | CH₃ | CF₃ | H | C(CH₃)=NOH |
| 230 | F | Cl | CH₃ | CF₃ | H | C(CH₃)=NOCH₃ |
| 231 | F | Cl | CH₃ | CF₃ | H | C(CH₃)=NOCH₂C≡CH |
| 232 | F | Cl | CH₃ | CF₃ | H | C(CH₃)=NOCH₂CO₂CH₃ |
| 233 | F | Cl | CH₃ | CF₃ | H | C(CH₃)=NOCH(CH₃)CO₂CH₃ |
| 234 | F | Cl | CH₃ | CF₃ | H | C(CH₃)=NOCH₂CH₂Cl |
| 235 | F | Cl | CH₃ | CF₃ | H | C(CH₃)=NO(CH₂)₃Cl |
| 236 | F | Cl | CH₃ | CF₃ | H | CH=NOH |
| 237 | F | Cl | CH₃ | CF₃ | H | CH=NOCH₃ |
| 238 | F | Cl | CH₃ | CF₃ | H | CH=NOCH₂CH=CH₂ |
| 239 | F | Cl | CH₃ | CF₃ | H | CH=NOCH₂C≡CH |
| 240 | H | Cl | CH₃ | CF₃ | H | COCH₃ |
| 241 | H | Cl | CH₃ | CF₃ | H | C(CH₃)=NOH |
| 242 | H | Cl | CH₃ | CF₃ | H | C(CH₃)=NOCH₃ |
| 243 | H | Cl | CH₃ | CF₃ | H | C(CH₃)=NOCH₂CO₂CH₃ |
| 244 | H | Cl | CH₃ | CF₃ | H | C(CH₃)=NOCH₂C≡CH |
| 245 | H | Cl | CH₃ | CF₃ | H | C(CH₃)=NOC₃H₇(iso) |
| 246 | H | Cl | CH₃ | CF₃ | H | C(CH₃)=NOC₅H₉(c) |
| 247 | F | Cl | CH₃ | CF₃ | H | 3,4,5,6-tetrahydrophthalimid-N-yl |
| 248 | H | Cl | CH₃ | CF₃ | H | 3,4,5,6-tetrahydrophthalimid-N-yl |
| 249 | H | Cl | CH₃ | CF₃ | H | NH₂ |
| 250 | F | Cl | CH₃ | CF₃ | H | SCH₂CO₂C₂H₅ |
| 251 | F | Cl | CH₃ | CF₃ | H | SCH₂CO₂C₃H₇(n) |
| 252 | F | Cl | CH₃ | CF₃ | H | SCH₂CO₂C₃H₇(iso) |
| 253 | F | Cl | CH₃ | CF₃ | H | SCH₂CO₂CH₂C₆H₅ |

TABLE 1-continued

| Compound No. | X | Y | $R_1$ | $R_2$ | $R_3$ | B |
|---|---|---|---|---|---|---|
| 254 | F | Cl | $CH_3$ | $CF_3$ | H | $SCH_2CO_2C_4H_9(n)$ |
| 255 | F | Cl | $CH_3$ | $CF_3$ | H | $SCH_2CO_2-CH_2CH=CH_2$ |
| 256 | F | Cl | $CH_3$ | $CF_3$ | H | $SCH_2CO_2CH_2CH_2CH=CH_2$ |
| 257 | F | Cl | $CH_3$ | $CF_3$ | H | $SCH_2CO_2CH_2CH_2OCH_3$ |
| 258 | F | Cl | $CH_3$ | $CF_3$ | H | $SCH_2CO_2C_5H_9(c)$ |
| 259 | F | Cl | $CH_3$ | $CF_3$ | H | $SCH_2CO_2C_6H_{11}(c)$ |
| 260 | H | Cl | $CH_3$ | $CF_3$ | H | $CH=CHCO_2CH_3$ |
| 261 | H | Cl | $CH_3$ | $CF_3$ | H | $NHCOCH_3$ |

TABLE 2

| Compound No. | X | $R_1$ | $R_2$ | $R_3$ | $R_4$ |
|---|---|---|---|---|---|
| 301 | F | $CH_3$ | $CH_3$ | H | $C_4H_9(sec)$ |
| 302 | F | $CH_3$ | $CF_3$ | H | $C_4H_9(sec)$ |
| 303 | F | $CH_3$ | $C_4H_9(tert)$ | H | $C_4H_9(sec)$ |
| 304 | H | $CH_3$ | $CF_3$ | H | $CH(CH_3)COOC_2H_5$ |
| 305 | F | $CH_3$ | $CF_3$ | H | $CH_3$ |
| 306 | F | $CH_3$ | $CF_3$ | H | $C_3H_7(iso)$ |
| 307 | F | $CH_3$ | $CF_3$ | H | $CH_2CH=CH_2$ |
| 308 | F | $CH_3$ | $CF_3$ | H | $CH_2C(Cl)=CH_2$ |
| 309 | F | $CH_3$ | $CF_3$ | H | $CH_2C\equiv CH$ |
| 310 | F | $CH_3$ | $CF_3$ | H | $CH(CH_3)C\equiv CH$ |
| 311 | F | $CH_3$ | $CF_3$ | H | $CH_2CN$ |
| 312 | F | $CH_3$ | $CF_3$ | H | $CH_2COOCH_3$ |
| 313 | F | $CH_3$ | $CF_3$ | H | $CH_2COOC_2H_5$ |
| 314 | F | $CH_3$ | $CF_3$ | H | $CH(CH_3)COOCH_3$ |
| 315 | F | $CH_3$ | $CF_3$ | H | $CH(CH_3)COOC_2H_5$ |
| 316 | F | $C_2H_5$ | $CF_3$ | H | $C_3H_7(iso)$ |
| 317 | F | $CH_2CH=CH_2$ | $CF_3$ | H | $C_3H_7(iso)$ |
| 318 | H | $CH_3$ | $CF_3$ | H | $C_4H_9(sec)$ |
| 319 | H | $CH_3$ | $CF_3$ | H | $C_3H_7(iso)$ |
| 320 | H | $CH_3$ | $CF_3$ | H | $CH_3$ |
| 321 | H | $CH_3$ | $CF_3$ | H | $CH_2CH=CH_2$ |
| 322 | H | $CH_3$ | $CF_3$ | H | $CH_2C(Cl)=CH_2$ |
| 323 | H | $CH_3$ | $CF_3$ | H | $CH_2C\equiv CH$ |
| 324 | H | $CH_3$ | $CF_3$ | H | $CH(CH_3)C\equiv CH$ |
| 325 | H | $CH_3$ | $CF_3$ | H | $CH_2CN$ |
| 326 | H | $CH_3$ | $CF_3$ | H | $CH_2COOCH_3$ |
| 327 | H | $CH_3$ | $CF_3$ | H | $CH_2COOC_2H_5$ |
| 328 | H | $CH_3$ | $CF_3$ | H | $CH(CH_3)COOCH_3$ |
| 329 | F | $CH_3$ | CN | H | $C_4H_9(sec)$ |
| 330 | F | $CH_3$ | $CF_2CF_3$ | H | $C_4H_9(sec)$ |
| 331 | F | $CH_3$ | $CF_2CF_2H$ | H | $C_4H_9(sec)$ |
| 332 | F | $CH_3$ | $CF_2Cl$ | H | $C_4H_9(sec)$ |
| 333 | F | $CH_3$ | $CF_2Cl$ | H | $C_3H_7(iso)$ |
| 334 | F | $CH_3$ | $CF_2Cl$ | H | $CH_2CH=CH_2$ |
| 335 | F | $CH_3$ | $CF_2Cl$ | H | $CH_2C\equiv CH$ |

TABLE 2-continued

| Compound No. | X | $R_1$ | $R_2$ | $R_3$ | $R_4$ |
|---|---|---|---|---|---|
| 336 | F | $CH_3$ | $CF_2Cl$ | H | $CH_2C\equiv N$ |
| 337 | F | $CH_3$ | $CF_2Cl$ | H | $CH_2CO_2CH_3$ |
| 338 | F | $CH_3$ | $CF_2Cl$ | H | $CH(CH_3)CO_2CH_3$ |

TABLE 3

| Compound No. | X | $R_1$ | $R_2$ | $R_3$ | $R_4$ |
|---|---|---|---|---|---|
| 401 | F | $CH_3$ | $CH_3$ | H | $CH_2C\equiv CH$ |
| 402 | F | $CH_3$ | $CF_3$ | H | $CH_2C\equiv CH$ |
| 403 | F | $CH_3$ | $C_4H_9(tert)$ | H | $CH_2C\equiv CH$ |
| 404 | F | $CH_2CH\equiv CH_2$ | $CF_3$ | H | $CH_2C\equiv CH$ |
| 405 | F | $C_2H_5$ | $CF_3$ | H | $CH_2C\equiv CH$ |
| 406 | F | $CH_3$ | $CF_3$ | H | $CH_3$ |
| 407 | F | $CH_3$ | $CF_3$ | H | $C_2H_5$ |
| 408 | F | $CH_3$ | $CF_3$ | H | $C_3H_7(iso)$ |
| 409 | F | $CH_3$ | $CF_3$ | H | $C_4H_9(sec)$ |
| 410 | F | $CH_3$ | $CF_3$ | H | $CH_2CH=CH_2$ |
| 411 | F | $CH_3$ | $CF_3$ | H | $CH(CH_3)C\equiv CH$ |
| 412 | F | $CH_3$ | $CF_3$ | H | $CH_2CN$ |
| 413 | F | $CH_3$ | $CF_3$ | H | $CH_2COOCH_3$ |
| 414 | F | $CH_3$ | $CF_3$ | H | $CH_2COOC_2H_5$ |
| 415 | F | $CH_3$ | $CF_3$ | H | $CH(CH_3)COOCH_3$ |
| 416 | F | $CH_3$ | $CF_3$ | H | $CH(CH_3)COOC_2H_5$ |
| 417 | H | $CH_2CH\equiv CH_2$ | $CH_3$ | H | $CH_2C\equiv CH$ |
| 418 | H | $CH_2CH\equiv CH_2$ | $CF_3$ | H | $CH_2C\equiv CH$ |
| 419 | H | $CH_3$ | $CF_3$ | H | $CH_3$ |
| 420 | H | $CH_3$ | $CF_3$ | H | $C_2H_5$ |
| 421 | H | $CH_3$ | $CF_3$ | H | $C_3H_7(iso)$ |
| 422 | H | $CH_3$ | $CF_3$ | H | $C_4H_9(sec)$ |
| 423 | H | $CH_3$ | $CF_3$ | H | $CH_2CH=CH_2$ |
| 424 | H | $CH_3$ | $CF_3$ | H | $CH_2C\equiv CH$ |
| 425 | H | $CH_3$ | $CF_3$ | H | $CH(CH_3)C\equiv CH$ |
| 426 | H | $CH_3$ | $CF_3$ | H | $CH_2CN$ |
| 427 | H | $CH_3$ | $CF_3$ | H | $CH_2COOCH_3$ |
| 428 | H | $CH_3$ | $CF_3$ | H | $CH_2COOC_2H_5$ |
| 429 | H | $CH_3$ | $CF_3$ | H | $CH(CH_3)COOCH_3$ |
| 430 | H | $CH_3$ | $CF_3$ | H | $CH(CH_3)COOC_2H_5$ |
| 431 | F | $CH_3$ | $CF_3$ | H | $CH(CH_3)CO_2C_5H_{11}(n)$ |
| 432 | F | $CH_3$ | $CF_3$ | H | $CH(CH_3)CN$ |
| 433 | F | $CH_3$ | $CF_3$ | H | $CH_2CH_2F$ |
| 434 | F | $CH_3$ | $CF_2CF_3$ | H | $CH_2C\equiv CH$ |

TABLE 3-continued

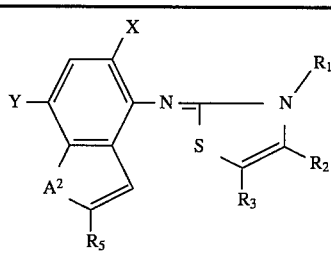

| Compound No. | X | R₁ | R₂ | R₃ | R₄ |
|---|---|---|---|---|---|
| 435 | F | $CH_3$ | $CF_2CF_2H$ | H | $CH_2C\equiv CH$ |
| 436 | F | $CH_3$ | $CF_2Cl$ | H | $CH_2C\equiv CH$ |
| 437 | F | $CH_3$ | $C_6H_5$ | H | $CH_2C\equiv CH$ |
| 438 | F | $CH_3$ | $CO_2C_2H_5$ | H | $CH_2C\equiv CH$ |
| 439 | F | $CH_3$ | $CO_2H$ | H | $CH_2C\equiv CH$ |
| 440 | F | $CH_3$ | $CONH_2$ | H | $CH_2C\equiv H$ |
| 441 | F | $CH_3$ | $CN$ | H | $CH_2C\equiv CH$ |

TABLE 4

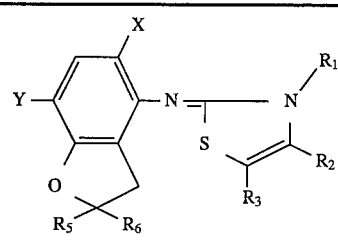

| Compound No. | X | Y | A² | R₁ | R₂ | R₃ | R₅ |
|---|---|---|---|---|---|---|---|
| 501 | F | Cl | O | $CH_3$ | $CF_3$ | H | $CH_3$ |
| 502 | F | Cl | O | $CH_3$ | $CF_3$ | H | $C_2H_5$ |
| 503 | F | Cl | O | $CH_3$ | $CF_3$ | H | $CH_2Br$ |
| 504 | F | Cl | O | $CH_3$ | $CH_3$ | H | $CH_3$ |
| 505 | F | Cl | O | $CH_3$ | $CH_3$ | H | $C_2H_5$ |
| 506 | F | Cl | O | $CH_3$ | $C_4H_9(tert)$ | H | $CH_3$ |
| 507 | F | Cl | O | $CH_3$ | $C_4H_9(tert)$ | H | $C_2H_5$ |
| 508 | F | F | O | $CH_3$ | $CF_3$ | H | $CH_3$ |
| 509 | F | F | O | $CH_3$ | $CF_3$ | H | $C_2H_5$ |
| 510 | F | F | O | $CH_3$ | $CF_3$ | H | $CH_2Br$ |
| 511 | F | Cl | S | $CH_3$ | $CF_3$ | H | $CH_3$ |
| 512 | F | Br | O | $CH_3$ | $CF_3$ | H | $CH_3$ |
| 513 | F | Cl | O | $C_2H_5$ | $CF_3$ | H | $CH_3$ |
| 514 | F | Cl | O | $CH_2CH=CH_2$ | $CF_3$ | H | $CH_3$ |
| 515 | H | Cl | O | $CH_3$ | $CF_3$ | H | $CH_3$ |
| 516 | H | Cl | O | $CH_3$ | $CF_3$ | H | $C_2H_5$ |
| 517 | H | Cl | O | $CH_3$ | $CF_3$ | H | $CH_2Br$ |
| 518 | H | Cl | O | $CH_3$ | $CH_3$ | H | $CH_3$ |
| 519 | H | Cl | O | $CH_3$ | $CH_3$ | H | $C_2H_5$ |
| 520 | H | Cl | O | $CH_3$ | $CH_3$ | H | $CH_2Br$ |
| 521 | H | Cl | O | $CH_3$ | $C_4H_9(tert)$ | H | $CH_3$ |
| 522 | H | Cl | O | $CH_3$ | $C_4H_9(tert)$ | H | $C_2H_5$ |
| 523 | H | Cl | O | $CH_3$ | $C_4H_9(tert)$ | H | $CH_2Br$ |

TABLE 5

| Compound No. | X | Y | R₁ | R₂ | R₃ | R₆ | R₅ |
|---|---|---|---|---|---|---|---|
| 601 | F | Cl | $CH_3$ | $CF_3$ | H | H | $CH_3$ |
| 602 | F | Cl | $CH_3$ | $CF_3$ | H | H | $CH_2OH$ |
| 603 | F | Cl | $CH_3$ | $CF_3$ | H | H | $CH_2OCH_2OCH_3$ |
| 604 | F | Cl | $CH_3$ | $CF_3$ | H | H | $CH_2OCOCH_3$ |
| 605 | F | Cl | $CH_3$ | $CF_3$ | H | H | $COOH$ |
| 606 | F | Cl | $CH_3$ | $CF_3$ | H | H | $COOCH_3$ |
| 607 | F | Cl | $CH_3$ | $CF_3$ | H | H | $CH_2Cl$ |
| 608 | F | Cl | $CH_3$ | $CF_3$ | H | $CH_3$ | $CH_3$ |
| 609 | F | Cl | $CH_3$ | $CF_3$ | H | $CH_3$ | $CH_2OH$ |
| 610 | F | Cl | $CH_3$ | $CF_3$ | H | $CH_3$ | $CH_2OCH_2OCH_3$ |
| 611 | F | Cl | $CH_3$ | $CF_3$ | H | $CH_3$ | $CH_2OCOCH_3$ |
| 612 | F | Cl | $CH_3$ | $CF_3$ | H | $CH_3$ | $COOH$ |
| 613 | F | Cl | $CH_3$ | $CF_3$ | H | $CH_3$ | $COOCH_3$ |
| 614 | F | Cl | $CH_3$ | $CF_3$ | H | $CH_3$ | $CH_2Cl$ |
| 615 | H | Cl | $CH_3$ | $CF_3$ | H | H | $CH_3$ |
| 616 | H | Cl | $CH_3$ | $CF_3$ | H | H | $CH_2OH$ |
| 617 | H | Cl | $CH_3$ | $CF_3$ | H | H | $CH_2OCH_2OCH_3$ |
| 618 | H | Cl | $CH_3$ | $CF_3$ | H | H | $CH_2OCOCH_3$ |
| 619 | H | Cl | $CH_3$ | $CF_3$ | H | H | $COOH$ |
| 620 | H | Cl | $CH_3$ | $CF_3$ | H | H | $COOCH_3$ |
| 621 | H | Cl | $CH_3$ | $CF_3$ | H | H | $CH_2Cl$ |
| 622 | H | Cl | $CH_3$ | $CF_3$ | H | $CH_3$ | $CH_3$ |
| 623 | H | Cl | $CH_3$ | $CF_3$ | H | $CH_3$ | $CH_2OH$ |
| 624 | H | Cl | $CH_3$ | $CF_3$ | H | $CH_3$ | $CH_2OCH_2OCH_3$ |
| 625 | H | Cl | $CH_3$ | $CF_3$ | H | $CH_3$ | $CH_2OCOCH_3$ |
| 626 | H | Cl | $CH_3$ | $CF_3$ | H | $CH_3$ | $COOH$ |
| 627 | H | Cl | $CH_3$ | $CF_3$ | H | $CH_3$ | $COOCH_3$ |
| 628 | H | Cl | $CH_3$ | $CF_3$ | H | $CH_3$ | $CH_2Cl$ |

In these tables, "(n)" refers to normal alkyl, "(i)" to isoalkyl and "(c)" to cycloalkyl.

Production Process M

The compound [2] as the starting compound for the production of the present compound can be produced by reacting an isothiocyanate derivative of the general formula:

Q-NCS          (19)

wherein Q is as defined above, with an amine derivative of the general formula:

$R_1$-$NH_2$          (20)

wherein $R_1$ is as defined above, or by reacting an aniline derivative of the general formula:

Q-$NH_2$          (21)

wherein Q is as defined above, with an isothiocyanate compound of the general formula:

$R_1$-NCS          (22)

wherein $R_1$ is as defined above.

These reactions are usually effected in a solvent. The reaction temperature is usually in the range of 0° to 200° C., and the reaction time is usually a moment to 48 hours. The compound [20] or [21] is usually used at an amount of 1 to 3 moles per mole of the compound [19] or [22], respectively.

Examples of the solvent to be used are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and diethylene glycol dimethyl ether; esters such as ethyl formate, ethyl acetate, butyl acetate and diethyl carbonate; nitro compounds such as nitroethane and nitrobenzene; nitriles such as acetonitrile and isobutyronitrile; tertiary amines such as pyridine, triethylamine, N,N-diethylaniline, tributylamine and N-methylmorphorine; acid an-tides such as formamide, N,N-dimethylformamide and acetamide; sulfur compounds such as dimethylsulfoxide and sulforane; water; or mixture thereof.

In this reaction, there is usually no need to use a base, but a base may be used in some cases. Examples of the base are organic bases such as pyridine, triethylamine and N,N-diethylaniline; and inorganic bases such as sodium hydroxide, potassium hydroxide, sodium carbonate, potassium carbonate and sodium hydride.

After completion of the reaction, the reaction mixture is poured into water, and the mixture is subjected to ordinary post-treatments such as extraction with an organic solvent and concentration. If necessary, it may be purified by a technique such as chromatography or recrystallization. Thus, the desired compound can be obtained.

The compounds [19] and [22] can be produced by reacting the corresponding aniline and the corresponding amine, respectively, with thiophosgene, or with carbon disulfide in the presence of a base, to give the corresponding dithiocarbamate, and then reacting the dithiocarbamate with a haloformate such as methyl chloroformate.

The compound [21] can be produced according to the processes as described in EP-61741-A, U.S. Pat. Nos. 4,670,046, 4,770,695, 4,709,049, 4,640,707, 5,030,760, 4,720,297, 5,169,431, 4,670,042, JP-A 1-168662 and JP-A 60-78959, or by the following production route N.

Production Route N

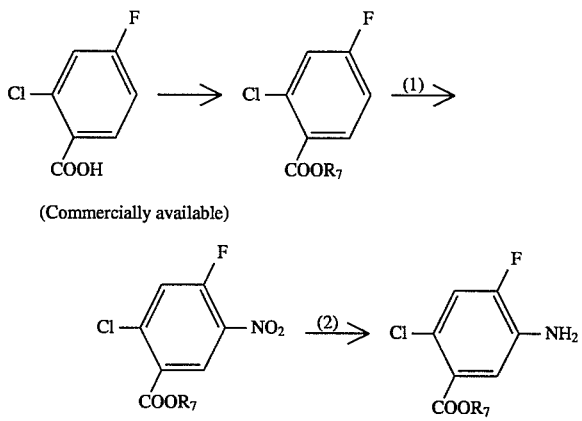

(Commercially available)

wherein $R_7$ is as defined above, and the steps (1) and (2) are the same as those of the Production Route C.

Production Process O

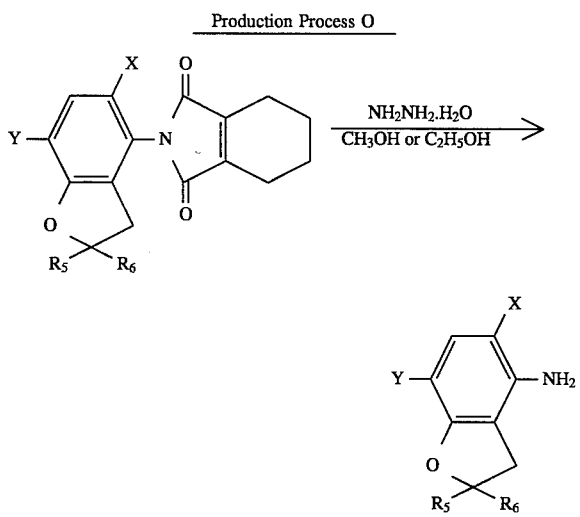

wherein X, Y, $R_5$ and $R_6$ are each as defined above, and the starting imide compound can be produced according to the process as described in WO 93/14073.

The present compounds have excellent herbicidal activity, and some of them exhibit excellent selectivity between crop plants and weeds. More particularly, the present compounds have herbicidal activity against various unfavorable weeds as recited below under the foliar treatment or soil treatment on upland fields.

Polygonaceae:

wild buckwheat (*Polygonum convolvulus*), pale smartweed (*Polygonum lapathifolium*), Pennsylvania smartweed (*Polygonum pensylvanicunz*), ladysthumb (*Polygonum persicaria*), curly dock (*Rumex crispus*), broadleaf dock (*Rumex obtusifolius*), Japanese knotweed (*Polygonum cuspidalum*)

Portulacaceae:

common purslane (*Portulaca oleracea*)

Caryophyllaceae:

common chickweed (*Stellaria media*)

Chenopodiaceae:

common lambsquarters (*Chenopodium album*), kochia (*Kochia scoparia*)

Amaranthaceae:

redroot pigweed (*Amaranthus retroflexus*), smooth pigweed (*Amaranthus hybridus*)

Crusiferae:

wild radish (*Raphantts raphanistrum*), wild mustard (*Sinapis arvensis*), shepherdspurse (*Capsella bursa-pastoris*)

Leguminosae:

hemp sesbania (*Sesbania exaltata*), sicklepod (*Cassia obtusifolia*), Horida beggarweed (*Desmodium tortuosum*), white clover (*Trifolium repens*)

Malvaceae:

velvetleaf (*Abutilon theophrasti*), prickly sida (*Sida spinosa*)

Violaceae:

field pansy (*Viola arvensis*), wild pansy (*Viola tricolor*)

Rubiaceae:

catchweed bedstraw (*cleavers*) (*Galium aparine*)

Convolvulaceae:

ivyleaf morningglory (*Ipomoea hederacea*), tall morningglory (*Ipomoea purpurea*), entireleaf moringglory (*Ipomoea hederacea var. integriuscula*), pitted morningglory (*Ipomoea lacunosa*), field bindweed (*Convolvuhts arvensis*)

Labiatae:

red deadnettle (*Lamium purpurerum*), henbit (*Lamium amplexicaule*)

Solanaceae:

jimsonweed (*Datura stramonitmz*), black nightshade (*Solanutn nigrum*)

Scrophulariaceae:

birdseye speedwell (*Veronica persica*), ivyleaf speedwell (*Veronica hederaefolia*)

Compositae:

common cocklebur (*Xanthium pensylvanicum*), common sunflower (*Helianthus annuus*), scentless chamomile (*Matricaria inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)

Boraginaceae:

field forget-me-not (*Myosotis arvensis*)

Asclepiadaceae:

common milkweed (*Asclepias syriaca*)

Euphorbiaceae:

sun spurge (*Euphorbia helioscopia*), spotted spurge (*Euphorbia maculata*)

Gramineae:

barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomifiorum*), Texas panicum (*Panicurn texanum*), shattercane (*Sorghum vulgare*)

Commelinaceae:

con-tmon dayflower (*Commelina communis*)

Equisetaceae:

field horsetail (*Equisetum arvense*)

Cyperaceae:

rice flatsedge (*Cypertts iria*), purple nutsedge (*Cypertts rotundus*), yellow nutsedge (*Cyperus esculentus*)

Further, some of the present compounds have no problematic phytotoxicity on main crops such as corn (*Zea mays*), wheat (*Triticum aestivum*), barley (*Hordeum vulgare*), rice (*Otyza sativa*), sorghum (*Sorghum bicolor*), soybean (*Glycine max*), cotton (*Gossypium spp.*), sugar beet (*Beta vulgaris*), peanut (*Arachis hypogaea*), sunflower (*Helianthus annuus*) and canola (*Brassica napus*); garden crops such as flowers and ornamental plants; and vegetable crops.

The present compounds can attain effective control of unfavorable weeds in the no-tillage cultivation. Further, some of them exhibit no problematic phytotoxicity on crop plants such as soybean, corn and wheat.

The present compounds have herbicidal activity against various unfavorable weeds as recited below under the flooding treatment on paddy fields.

Gramineae:

barnyardgrass (*Echinochloa oryzicola*, *Echinochloa crttsgalli*)

Scrophulariaceae:

common falsepimpernel (*Lindernia procumbens*)

Lythraceae:

*Rotala indica*, *Ammannia multiflora*

Elatinaceae:

*Elatine triandra*

Cyperaceae:

smallflower umbrellaplant (*Cyperus difformis*), hardstem bulrush (*Scirpus juncoides*), needle spikerush (*Eleocharis acicularis*), *Cypertts serolinus*, *Eleocharis kuroguwai*

Pontederiaceae:

*Monochoria vaginalis*

Alismataceae:

*Sagittaria pygmaea, Sagittaria trfolia, Alisma canaliculatum*

Potamogetonaceae:

roundleaf pondweed (*Potamogeton distinctus*)

Umbelliferae:

*Oenanthe javanica*

Further, some of the present compounds have no problematic phytotoxicity on transplanted paddy rice or directly-sowed paddy rice.

The present compounds can attain effective control of various unfavorable weeds in orchards, grasslands, lawns, forests, waterways, canals or other non-cultivated lands.

When the present compound is used as an active ingredient of herbicides, it is usually formulated by mixing with solid or liquid carriers or diluents, surfactants and other auxiliary agents into conventional types of formulation, such as emulsifiable concentrates, wettable powders, flowables, granules, concentrated emulsion, waterdispersible granules and solutions.

These formulations each may contain at least one of the present compounds as an active ingredient at art amount of 0.001% to 90% by weight, preferably 0.01% to 80% by weight, based on the total weight of each formulation.

Examples of the solid carrier or diluent are fine powders or granules of the following materials: mineral matters such as kaolin clay, attapulgite clay, bentonite, terra alba, pyrophyllite, talc, diatomaceous earth and calcite; organic substances such as walnut shell powder; water-soluble organic substances such as urea; inorganic salts such as ammonium sulfate; and synthetic hydrous silica. Examples of the liquid carrier or diluent are aromatic hydrocarbons such as methylnaphthalene, phenylxylylethane and alkylbenzenes (e.g., xylene); alcohols such as isopropanol, ethylene glycol and 2-ethoxyethanol; esters such as phthalic acid dialkyl esters; ketones such as acetone, cyclohexanone and isophorone; mineral oils such as machine oil; vegetable oils such as soybean oil and cotton seed oil; dimethylsulfoxide, N,N-dimethylformamide, acetonitrile, N-methylpyrrolidone, water, and the like.

Examples of the surfactant used for emulsification, dispersing or spreading are surfactants of the anionic type, such as alkylsulfates, alkylsulfonates, alkylarylsulfonates, dialkylsulfosuccinates and phosphates of polyoxyethylene alkylaryl ether; and surfactants of the nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent used for formulation are ligninsulfonates, alginates, polyvinyl alcohol, gum arabic, carboxymethyl cellulose (CMC) and isopropyl acid phosphate (PAP).

The present compound is usually formulated into any suitable type of formulation and used for pre-emergence or post-emergence control of unfavorable weeds by soil treatment, foliar treatment or flooding treatment in upland fields or paddy fields. The soil treatment includes soil surface treatment and soil incorporation. The foliar treatment includes application over the plants and directed application to the weeds to keep any chemical off the crop foliage.

Further, the present compound may be used together with other herbicides to enhance its herbicidal activity. Moreover, the present compound may also be used in admixture with insecticides, acaricides, nematocides, fungicides, plant growth regulators, fertilizers, soil improver, and the like.

When the present compound is used as an active ingredient of herbicides, the application amount is usually in the range of 0.1 to 5000 g, preferably 1 to 1000 g, per hectare, although it may vary depending upon the prevailing weather conditions, formulation type used, application timing, application method, soil involved, crop and weed species, and the like. In the case of emulsifiable concentrates, wettable powders, flowables, concentrated emulsions, water-dispersible granules or solutions, the formulation is usually applied at a prescribed amount after diluted with water having a volume of about 10 to 10000 liters per hectare, if necessary, with the addition of an adjuvant such as a spreading agent. In the case of granules, some types of flowables or solutions, the formulation is usually applied without any dilution.

Examples of the adjuvant are, in addition to the above-described surfactants, polyoxyethylene resin acids (esters), ligninsulfonates, abietates, dinaphthylmethanedisulfonates, crop oil concentrates and vegetable oils such as soybean oil, corn oil, cotton seed oil and sunflower oil.

The present compound can be used as an active ingredient of harvesting aids such as defoliants and desiccating agents for cotton (*Gossypium spp.*) and desiccating agents for potato (*Solanum tuberosum*). In that case, the present compound is usually formulated in the same manner as the case where it is used as an active ingredient of herbicides, and used alone or in admixture with other harvesting aids for foliar treatment before the harvesting of crops.

The present invention will be further illustrated by the following production examples, formulation examples and test examples, which are not to be construed to limit the scope of the invention.

The following will describe production examples of the present compounds. In these production examples, the present compounds are designated by the corresponding compound numbers as shown in Tables 1 to 5.

The compound [2] as the starting material was selected from the following compounds 2-1 to 2-15.

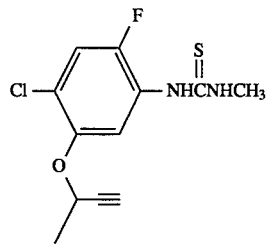

(2-1)

(2-2) 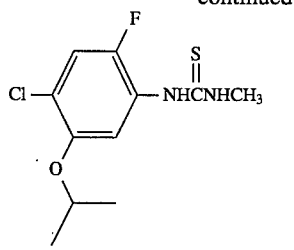
(2-3) 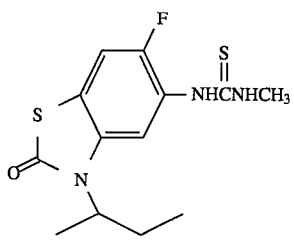
(2-4) 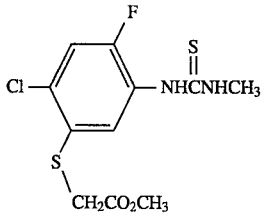
(2-5) 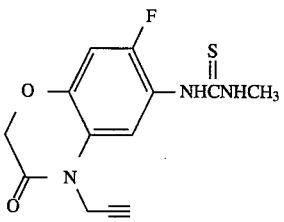
(2-6) 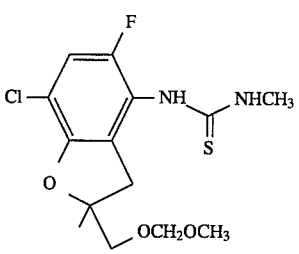
(2-7) 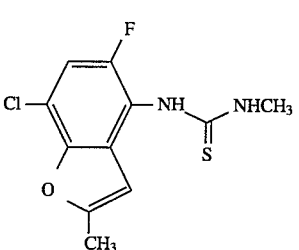
(2-8) 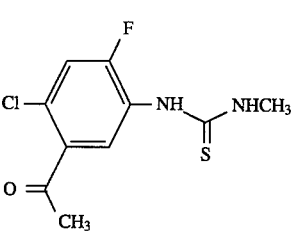
(2-9) 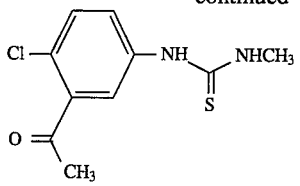
(2-10) 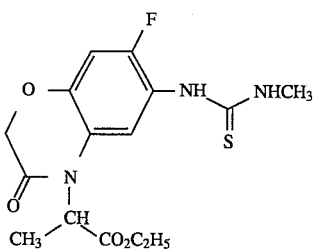
(2-11) 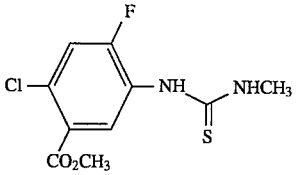
(2-12) 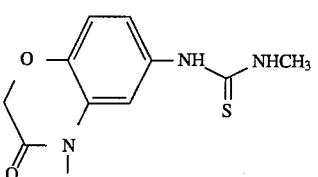
(2-13) 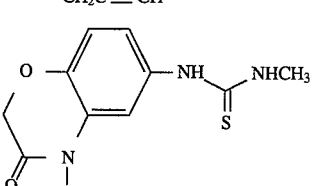
(2-14) 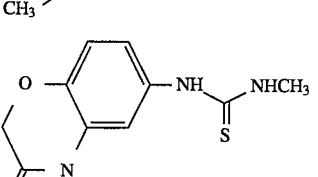
(2-15) 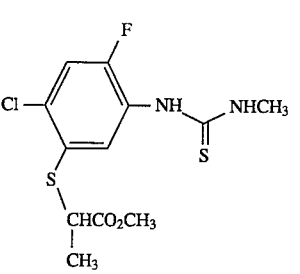
Production Example 1
To a suspension containing 14 g of the compound 2-5 and 4.0 g of sodium acetate in 150 ml of toluene was added 9.6 g of 1,1,1-trifluoro-3-bromoacetone, and the reaction was allowed to proceed at 50° C. for 3 hours. The reaction mixture was poured into water, followed by phase separation. The organic layer was washed with water, dried with magnesium sulfate, and concentrated. The residue thus obtained was mixed with 70 ml of concentrated sulfuric acid, followed by stirring for 1 hour. After completion of the reaction, the reaction mixture was poured onto ice, which was then extracted with ethyl acetate. The organic layer was washed with water, dried with magnesium sulfate, and concentrated. The residue thus obtained was subjected to silica gel chromatography (eluent; hexane:ethyl acetate= 5:1), which afforded 9.2 g of the compound 402.

Production Example 2

To a suspension containing 1.4 g of the compound 2-6 and 0.5 g of sodium acetate in 20 ml of toluene was added 1.0 g of 1,1,1-trifluoro-3-bromoacetone, and the mixture was heated under reflux for 2 hours. After completion of the reaction, the reaction mixture was poured into water, followed by phase separation. The organic layer was washed with water, dried with magnesium sulfate, and concentrated. The residue thus obtained was mixed with 10 ml of the concentrated sulfuric acid, followed by stirring. The reaction mixture was poured onto ice, which was then extracted with ethyl acetate. The organic layer was washed with water, dried with magnesium sulfate, and concentrated. The residue thus obtained was subjected to silica gel chromatography (eluent; hexane:ethyl acetate=5:1), which afforded 0.2 g of the compound 609.

Production Example 3

To a suspension containing 1.4 g of the compound 2-7 and 0.5 g of sodium acetate in 20 ml of toluene was added 1.0 g of 1,1,1-trifluoro-3-bromoacetone, and the mixture was heated under reflux for 2 hours. After completion of the reaction, the reaction mixture was poured into water, followed by phase separation. The organic layer was washed with water, dried with magnesium sulfate, and concentrated. The residue thus obtained was mixed with 10 ml of the concentrated sulfuric acid, followed by stirring. The reaction mixture was poured onto ice, which was then extracted with ethyl acetate. The organic layer was washed with water, dried with magnesium sulfate, and concentrated. The residue thus obtained was subjected to silica gel chromatography (eluent; hexane:ethyl acetate=5:1), which afforded 1.1 g of the compound 501.

Production Example 4

First, 0.4 g of the compound 2-5 and 0.29 g of 1,1,1-trifluoro-3-bromoacetone were heated under reflux in 15 ml of toluene for 3 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=5:1), which afforded 0.13 g of the compound 402.

Production Example 5

First, 0.4 g of the compound 2-4 and 0.29 g of 1,1,1-trifluoro-3-bromoacetone were heated under reflux in 10 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=10:1), which afforded 0.15 g of the compound 104.

Production Example 6

First, 1.0 g of the compound 2-1 and 0.39 g of chloroacetone were heated under reflux in 15 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=1), which afforded 0.91 g of the compound 101.

Production Example 7

First, 0.5 g of the compound 2-3 and 0.15 g of chloroacetone were heated under reflux in 10 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=2:1), which afforded 0.15 g of the compound 301.

Production Example 8

First, 0.4 g of the compound 2-4 and 0.14 g of chloroacetone were heated under reflux in 10 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=3.5:1), which afforded 0.19 g of the compound 102.

Production Example 9

First, 0.4 g of the compound 2-5 and 0.14 g of chloroacetone were heated under reflux in 10 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=3.5:1), which afforded 0.16 g of the compound 401.

Production Example 10

First, 1.0 g of the compound 2-1 and 0.67 g of 1,1,1-trifluoro-3-bromoacetone were heated under reflux in 15 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=10:1), which afforded 0.35 g of the compound 103.

Production Example 11

First, 0.5 g of the compound 2-3 and 0.31 g of 1,1,1-trifluoro-3-bromoacetone were heated under reflux in 10 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=4:1), which afforded 0.15 g of the compound 302.

Production Example 12

First, 0.5 g of the compound 2-3 and 0.36 g of 1,1,1-trimethyl-3-bromoacetone were heated under reflux in 10 ml of toluene for 3 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=5:1), which afforded 0.31 g of the compound 303.

Production Example 13

First, 0.4 g of the compound 2-4, 0.23 g of 1,1,1-trimethyl-3-bromoacetone and 0.1 g of sodium acetate were heated under reflux in 10 ml of isopropanol for 3 hours. After completion of the reaction, the reaction mixture was poured into water, followed by addition of saturated aqueous sodium bicarbonate solution, and the mixture was extracted with ethyl acetate. The organic layer was dried with magnesium sulfite and concentrated. The residue thus obtained was subjected to silica gel chromatography (eluent; hexane:ethyl acetate=4:1), which afforded 0.23 g of the compound 105.

Production Example 14

First, 0.4 g of the compound 2-5, 0.25 g of 1,1,1-trimethyl-3-bromoacetone and 0.12 g of sodium acetate were heated under reflux in 10 ml of isopropanol for 3 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=4:1), which afforded 0.15 g of the compound 403.

Production Example 15

First, 0.5 g of the compound 2-2 and 0.18 g of chloroacetone were heated under reflux in 10 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=3:1), which afforded 0.23 g of the compound 106.

Production Example 16

First, 0.5 g of the compound 2-2 and 0.36 g of 1,1,1-trimethyl-3-bromoacetone were heated under reflux in 10 ml of toluene for 2 hours. After completion of the reaction, the reaction mixture was poured into water, followed by addition of saturated aqueous sodium bicarbonate solution, and the mixture was extracted with ethyl acetate. The organic layer was dried with magnesium sulfate and concentrated. The residue thus obtained was subjected to silica gel chromatography (eluent; hexane:ethyl acetate=3:1), which afforded 0.54 g of the compound 107.

Production Example 17

First, 6.0 g of the compound 108 was added to 50 ml of sulfuric acid at room temperature, and the mixture was stirred for 2 hours. After completion of the reaction, the reaction mixture was poured onto ice, which was then extracted with diethyl ether. The organic layer was washed with water, dried with magnesium sulfate, and concentrated, which afforded 3.82 g of the compound 109.

Production Example 18

To 5 ml of dimethylformamide (DMF) were added 0.5 g of the compound 109 and 0.3 g of potassium carbonate, and the mixture was stirred for 15 minutes. Then, 0.2 g of methyl chloroacetate was added thereto, and the mixture was stirred at 40°–50° C. for 1 hour. After completion of the reaction, the reaction mixture was poured into water, which was then extracted with diethyl ether. The organic layer was washed with water, dried with magnesium sulfate, and concentrated. The residue thus obtained was subjected to silica gel chromatography (eluent; hexane:ethyl acetate=4:1), which afforded 0.42 g of the compound 111.

Production Example 19

To 5 ml of dimethylformamide were added 0.5 g of the compound 109 and 0.3 g of potassium carbonate, and the mixture was stirred for 15 minutes. Then, 0.33 g of ethyl 2-bromopropionate was added thereto, and the mixture was stirred at 40°–50° C. for 1 hour. After completion of the reaction, the reaction mixture was poured into water, which was then extracted with diethyl ether. The organic layer was washed with water, dried with magnesium sulfate, and concentrated. The residue thus obtained was subjected to silica gel chromatography (eluent; hexane:ethyl acetate=5:1), which afforded 0.5 g of the compound 110.

Production Example 20

To 5 ml of dimethylformamide were added 0.5 g of the compound 109 and 0.3 g of potassium carbonate, and the mixture was stirred for 15 minutes. Then, 0.2 g of 2,3-dichloro-1-propene was added thereto, and the mixture was stirred at 40°–50° C. for 1 hour. After completion of the reaction, the reaction mixture was poured into water, which was then extracted with diethyl ether. The organic layer was washed with water, dried with magnesium sulfate, and concentrated. The residue thus obtained was subjected to silica gel chromatography (eluent; hexane:ethyl acetate=5:1), which afforded 0.4 g of the compound 112.

Production Example 21

To 5 ml of dimethylformamide (DMF) were added 0.5 g of the compound 109 and 0.3 g of potassium carbonate, and the mixture was stirred for 15 minutes. Then, 0.22 g of allyl bromide was added thereto, and the mixture was stirred at 40°–50° C. for 1 hour. After completion of the reaction, the reaction mixture was poured into water, which was then extracted with diethyl ether. The organic layer was washed with water, dried with magnesium sulfate, and concentrated. The residue thus obtained was subjected to silica gel chromatography (eluent; hexane:ethyl acetate=4:1), which afforded 0.48 g of the compound 113.

Production Example 22

To 5 ml of dimethylformamide were added 0.5 g of the compound 109 and 0.3 g of potassium carbonate, and the mixture was stirred for 15 minutes. Then, 0.22 g of bromoacetonitrile was added thereto, and the mixture was stirred at 40°–50° C. for 1 hour. After completion of the reaction, the reaction mixture was poured into water, which was then extracted with diethyl ether. The organic layer was washed with water, dried with magnesium sulfate, and concentrated. The residue thus obtained was subjected to silica gel chromatography (eluent; hexane:ethyl acetate= 6:1), which afforded 0.21 g of the compound 114.

Production Example 23

To 5 ml of dimethylformamide were added 0.5 g of the compound 109 and 0.3 g of potassium carbonate, and the mixture was stirred for 15 minutes. Then, 0.22 g of propargyl bromide was added thereto, and the mixture was stirred for 1 hour. After completion of the reaction, the reaction mixture was poured into water, which was then extracted with diethyl ether. The organic layer was washed with water, dried with magnesium sulfate, and concentrated. The residue thus obtained was subjected to silica gel chromatography (eluent; hexane:ethyl acetate=6:1), which afforded 0.41 g of the compound 115.

Production Example 24

First, 10 g of 2-(4-chloro-2-fluorophenyl)imino-3-methyl-4-trifluoromethylthiazoline was added to 50 ml of concentrated sulfuric acid cooled in ice, to which 2.1 g of fuming nitric acid was added, and the mixture was stirred for 1 hour. After completion of the reaction, the reaction mixture was poured onto ice and neutralized with aqueous sodium hydroxide solution, which was then extracted with ethyl acetate. The organic layer was dried with magnesium sulfate and concentrated. The residue thus obtained was subjected to silica gel chromatography (eluent; hexane:ethyl acetate= 10:1), which afforded 3.2 g of the compound 122.

Production Example 25

First, 19 g of the compound a-3 obtained in Reference Example 1 below and 10 g of 1,1,1-trifluoro-3-bromoacetone were heated in 200 nil of toluene for I hour, and the solvent was removed by evaporation. The residue thus obtained was mixed with 150 ml of concentrated sulfuric acid, and the mixture was stirred for 3 hours. After completion of the reaction, the reaction mixture was poured onto ice, which was then extracted with ethyl acetate. The organic layer was dried with magnesium sulfate and concentrated. The residue thus obtained was subjected to silica gel chromatography (eluent; hexane:ethyl acetate=6:1), which afforded 21 g of the compound 247.

Production Example 26

First, 21 g of the compound 247 was dissolved in 150 ml of ethanol, to which 2.5 g of hydrazine hydrate was added, and the mixture was heated under reflux for 2 hours. After completion of the reaction, the reaction mixture was cooled to room temperature and filtered with Celitc. The filtrate was concentrated. The residue thus obtained was subjected to silica gel chromatography (eluent; hexane:ethyl acetate= 5:1), which afforded 13.3 g of the compound 211.

Production Example 27

First, 1.0 g of the compound 211, 0.72 g of methyl chlorosulfonyloxyacetate and 0.7 g of potassium carbonate were added to 20 ml of chloroform, and the mixture was stirred at room temperature for 4 hours. After completion of the reaction, the reaction mixture was poured into water, which was then extracted with ethyl acetate. The organic layer was dried with magnesium sulfate and concentrated. The residue thus obtained was subjected to silica gel chromatography (eluent; hexane:ethyl acetate=5:1), which afforded 0.4 g of the compound 142.

Production Example 28

First, 1.7 g of the compound 211, 1.1 g of ethyl 2-chlorosulfonyloxypropionate and 1.0 g of potassium carbonate were added to 30 ml of chloroform, and the mixture was stirred at room temperature for 4 hours. After completion of the reaction, the reaction mixture was poured into water, which was then extracted with ethyl acetate. The organic layer was dried with magnesium sulfate and concentrated. The residue thus obtained was subjected to silica gel chromatography (eluent; hexane:ethyl acetate=5:1), which afforded 0.31 g of the compound 146.

Production Example 29

First, 0.5 g of the compound 211 and 0.18 g of methanesulfonyl chloride were added to 4 ml of pyridine, and the mixture was stirred at room temperature for 1 hour. After completion of the reaction, the reaction mixture was poured into water, which was then extracted with diethyl ether. The organic layer was washed with diluted hydrochloric acid, dried with magnesium sulfate, and concentrated, which afforded 0.48 g of the compound 147.

Production Example 30

In this example, 0.5 g of the compound 211 and 0.28 g of 2,2,2-trifluoroethanesulfonyl chloride were added to 4 ml of pyridine, and the mixture was subjected to the same procedures as described in Production Example 29, which afforded 0.43 g of the compound 149.

Production Example 31

In this example, 1.3 g of the compound 211 and 0.62 g of chloromethanesulfonyl chloride were added to 10 ml of pyridine, and the mixture was subjected to the same procedures as described in Production Example 29, which afforded 0.93 g of the compound 150.

Production Example 32

In this example, 2.9 g of the compound a-5 obtained according to Reference Example 2 below and 1.5 g of 1,1,1-trifluoro-3-bromoacetone were subjected to the same procedures as described in Production Example 25, which afforded 3.1 g of the compound 248. The subsequent same procedures as described in Production Example 26 gave 2.0 g of the compound 249.

Production Example 33

In this example, 1.0 g of the compound 249, 0.85 g of ethyl 2-chlorosulfonyloxypropionate and 0.75 g of potassium carbonate were added to 20 ml of chloroform, and the mixture was subjected to the same procedures as described in Production Example 28, which afforded 0.5 g of the compound 191.

Production Example 34

In this example, 0.5 g of the compound 249 and 0.19 g of methanesulfonyl chloride were added to 5 ml of pyridine, and the mixture was subjected to the same procedures as described in Production Example 29, which afforded 0.42 g of the compound 192.

Production Example 35

In this example, 0.5 g of the compound 249 and 0.24 g of methanesulfonyl chloride were added to 5 ml of pyridine, and the mixture was subjected to the same procedures as described in Production Example 29, which afforded 0.51 g of the compound 194.

Production Example 36

First, 0.3 g of the compound 211 and 0.1 g of acetic anhydride were added to 5 ml of acetic acid, and the mixture was stirred at room temperature for 2 hours. After completion of the reaction, the reaction mixture was poured into water, which was then extracted with diethyl ether. The organic layer was washed with saturated aqueous sodium bicarbonate solution, dried with magnesium sulfate, and concentrated, which afforded 0.27 g of the compound 212.

Production Example 37

In this example, 0.3 g of the compound 211 and 0.17 g of chloroacetic anhydride were added to 5 ml of acetic acid, and the mixture was subjected to the same procedures as described in Production Example 36, which afforded 0.25 g of the compound 213.

Production Example 38

In this example, 0.3 g of the compound 211 and 0.2 g of trifluoroacetic anhydride were added to 5 ml of acetic acid, and the mixture was subjected to the same procedures as described in Production Example 36, which afforded 0.21 g of the compound 214.

Production Example 39

First, 5.0 g of the compound 2-8 and 3.8 g of 1,1,1-trifluoro-3-bromoacetone were added to 100 ml of toluene, and the mixture was heated under reflux for 1 hour. Then, the reaction mixture was poured into water, followed by phase separation. The organic layer was washed with saturated aqueous sodium bicarbonate solution, dried with magnesium sulfate and concentrated. The residue thus obtained was dissolved in 50 ml of sulfuric acid, and the mixture was stirred for 2 hours. After completion of the reaction, the reaction mixture was poured into ice water, which was then extracted with ethyl acetate. The organic layer was washed with saturated aqueous sodium bicarbonate solution, dried with magnesium sulfate, and concentrated. The residue thus obtained was subjected to silica gel chromatography (eluent; hexane:ethyl acetate=5:1), which afforded 4.1 g of the compound 228.

Production Example 40

First, 7.0 g of the compound 228 was dissolved in 100 ml of ethanol, to which 2.2 g of hydroxylamine hydrochloride and 2.2 g of triethylamine were added, and the mixture was heated under reflux for 2 hours. After completion of the reaction, the reaction mixture was poured into water, which was then extracted with ethyl acetate. The organic layer was washed with water, dried with magnesium sulfate, and concentrated, which afforded 4.05 g of the compound 229.

Production Example 41

First, 1.0 g of the compound 229, 0.32 g of methyl chloroacetate and 0.6 g of potassium carbonate were added to 10 ml of dimethylformamide, and the mixture was stirred at 50° C. for 2 hours. After completion of the reaction, the reaction mixture was poured into water, which was then extracted with diethyl ether. The organic layer was washed with water, dried with magnesium sulfate, and concentrated. The residue thus obtained was subjected to silica gel chromatography (eluent; hexane:ethyl acetate=5:1), which afforded 0.45 g of the compound 232.

Production Example 42

In this example, 5.2 g of the compound 2-9 and 4.1 g of 1,1,1-trifluoro-3-bromoacetone were added to 100 ml of toluene, and the mixture was subjected to the same procedures as described in Production Example 39, which afforded 4.4 g of the compound 240.

Production Example 43

In this example, 4.0 g of the compound 240 was dissolved in 100 ml of ethanol, to which 1.28 g of hydroxylamine hydrochloride and 1.6 g of triethylamine were added, and the mixture was subjected to the same procedures as described in Production Example 40, which afforded 4.05 g of the compound 241.

Production Example 44

First, 2.0 g of the compound 241 and 0.6 g of methyl chloroacetate were added to 20 ml of dimethylformamide, and the mixture was subjected to the same procedures as described in Production Example 41, which afforded 1.62 g of the compound 243.

Production Example 45

First, 2.2 g of the compound 2-11 and 2 ml of 1,1,1-trifluoro-3-bromoacetone were added to 30 ml of toluene, and the mixture was heated under reflux for 4 hours. Then, the reaction mixture was poured into water, which was then extracted with ethyl acetate. The organic layer was washed with saturated aqueous sodium carbonate solution, dried with magnesium sulfate, and concentrated. The residue thus obtained was mixed with 20 ml of concentrated sulfuric acid, and the mixture was stirred at room temperature for 30 minutes. After completion of the reaction, the reaction mixture was poured onto ice, which was then extracted with ethyl acetate. The organic layer was dried with magnesium sulfate and concentrated. The residue thus obtained was subjected to silica gel chromatography (eluent; hexane:ethyl acetate=6:1), which afforded 1.8 g of the compound 118.

Production Example 46

First, 1.1 g of the compound 118 was dissolved in a mixed solvent of 7 ml of 1,4-dioxane and 2 ml of water, to which 0.2 g of potassium hydroxide was added, and the mixture was stirred at room temperature for 14 hours. After completion of the reaction, 5 ml of concentrated hydrochloric acid was added to the reaction mixture while ice cooling, and the mixture was extracted with ethyl acetate. The organic layer was washed with water, dried with magnesium sulfate, and concentrated, which afforded 1.0 g of the compound 117.

Production Example 47

First, 0.45 g of the compound 117 was dissolved in 5 ml of thionyl chloride, and the solution was heated under reflux for 2 hours. After completion of the reaction, the reaction mixture was concentrated. The residue thus obtained was dissolved in 5 ml of chloroform, to which 1 ml of pyridine and 0.5 ml of ethanol were added, and the mixture was stirred at room temperature for 3 hours. After completion of the reaction, the reaction mixture was poured into water, which was then extracted with ethyl acetate. The organic layer was dried with magnesium sulfate and concentrated. The residue thus obtained was subjected to preparative thin layer chromatography (eluent; hexane:ethyl acetate=10:1), which afforded 0.31 g of the compound 223.

Production Example 48

In this example, 0.21 g of the compound 119 was obtained in the same manner as described in Production Example 47, except that isopropyl alcohol was used in place of ethanol.

Production Example 49

In this example, 4.0 g of the compound 2-7 and 2.8 g of 1,1,1-trifluoro-3-bromoacetone were added to 100 ml of toluene, and the mixture was subjected to the same procedures as described in Production Example 39, which afforded 3.8 g of the compound 501.

Production Example 50

In this example, 1.4 g of the compound 2-6 and 1.0 ml of 1,1,1-trifluoro-3-bromoacetone were added to 100 ml of toluene, and the mixture was subjected to the same procedures as described in Production Example 39, which afforded 0.2 g of the compound 609.

Production Example 51

In this example, 0.8 g of the compound 2-5 and 0.76 g of 1,1,1,2,2-pentafluoro-4-bromo-3-butanone were added to 100 ml of toluene, and the mixture was subjected to the same procedures as described in Production Example 39, which afforded 0.2 g of the compound 434.

Production Example 52

In this example, 0.9 g of the compound 2-3 and 0.7 g of 1,1,1,2,2-pentafluoro-4-bromo-3-butanone were added to 100 ml of toluene, and the mixture was subjected to the same procedures as described in Production Example 39, which afforded 0.89 g of the compound 330.

Production Example 53

First, 2.25 g of the compound 2-3 and 1.7 g of ethyl 2,4-dichloro-4,4-difluoroacetoacetate were added to 30 ml of isopropanol, and the mixture was heated under reflux for 2 hours. The reaction mixture was concentrated, to which 30 ml of 80% sulfuric acid was added, and the mixture was heated under reflux for 10 hours. After completion of the reaction, the reaction mixture was poured onto ice, which was then neutralized with aqueous sodium hydroxide solution and extracted with ethyl acetate. The organic layer was dried with magnesium sulfate and concentrated. The residue thus obtained was subjected to silica gel chromatography (eluent; hexane:ethyl acetate=5:1), which afforded 0.25 g of the compound 332.

Production Example 54

First, 4.1 g of the compound 2-12 and 3.2 g of 1,1,1-trifluoro-3-bromoacetone were added to 100 ml of toluene, and the mixture was heated under reflux for 2 hours. After completion of the reaction, the reaction mixture was poured into water, to which saturated aqueous sodium bicarbonate solution was added, and the mixture was extracted with ethyl acetate. The organic layer was dried with magnesium sulfate and concentrated. The residue thus obtained was subjected to silica gel chromatography (eluent; hexane:ethyl acetate= 3:1), which afforded 1.47 g of the compound 424.

Production Example 55

First, 2.1 g of the compound 2-13 and 1.5 g of 1,1,1-trifluoro-3-bromoacetone were added to 50 ml of toluene, and the mixture was heated under reflux for 2 hours. After completion of the reaction, the reaction mixture was poured into water, to which saturated aqueous sodium bicarbonate solution was added, and the mixture was extracted with ethyl acetate. The organic layer was dried with magnesium sulfate and concentrated. The residue thus obtained was subjected to silica gel chromatography (eluent; hexane:ethyl acetate= 3:1), which afforded 0.92 g of the compound 425.

Production Example 56

First, 1.9 g of the compound 2-14 and 1.4 g of 1,1,1-trifluoro-3-bromoacetone were added to 50 ml of toluene, and the mixture was heated under reflux for 2 hours. After completion of the reaction, the reaction mixture was poured into water, to which saturated aqueous sodium bicarbonate solution was added, and the mixture was extracted with ethyl acetate. The organic layer was dried with magnesium sulfate and concentrated. The residue thus obtained was subjected to silica gel chromatography (eluent; hexane:ethyl acetate= 3:1), which afforded 0.34 g of the compound 412.

Production Example 57

First, 3.0 g of the compound 2-5 and 1.7 g of α-chloroacetophenone were added to 50 ml of toluene, and the mixture was heated under reflux for 3 hours. After completion of the reaction, the reaction mixture was poured into water, to which saturated aqueous sodium bicarbonate solution was added, and the mixture was extracted with ethyl acetate. The organic layer was dried with magnesium sulfate and concentrated. The residue thus obtained was subjected to silica gel chromatography (eluent; hexane:ethyl acetate= 3:1), which afforded 2.6 g of the compound 437.

Production Example 58

First, 4.0 g of the compound 2-5 and 3.2 g of ethyl bromopyruvate were added to 200 ml of toluene, and the mixture was heated under reflux for 2 hours. After completion of the reaction, the reaction mixture was poured into water, to which saturated aqueous sodium bicarbonate solution was added, and the mixture was extracted with ethyl acetate. The organic layer was dried with magnesium sulfate and concentrated. The residue thus obtained was subjected to silica gel chromatography (eluent; hexane:ethyl acetate= 3:1), which afforded 2.7 g of the compound 438.

Production Example 59

First, 2.7 g of the compound 438 and 0.50 g of sodium hydroxide were added to 100 ml of a mixed solvent (water: 1,4-dioxane=1:1), and the mixture was stirred at room temperature for 2 hours. After completion of the reaction, the reaction mixture was neutralized with 1 N hydrochloric acid and poured into water, which was then extracted with ethyl acetate. The organic layer was dried with magnesium sulfate and concentrated, which afforded 1.7 g of the compound 439.

Production Example 60

To 0.50 g of the compound 439 was added 10 ml of thionyl chloride, and the reaction was allowed to proceed at 50° C. for 2 hours. The reaction mixture was concentrated, and the concentrate was suspended in isopropanol, into which ammonia gas was introduced at room temperature. The reaction mixture was poured into water, which was then extracted with ethyl acetate. The organic layer was dried with magnesium sulfate and concentrated, which afforded 0.40 g of the compound 440.

Production Example 61

First, 0.50 g of the compound 440 and 0.50 g of thionyl chloride were added to 15 ml of dimethylformamide, and the reaction was allowed to proceed at room temperature for 3 hours. After completion of the reaction, the reaction mixture was poured onto ice, which was then extracted with ethyl acetate. The organic layer was washed with saturated aqueous sodium bicarbonate solution, dried with magnesium sulfate, and concentrated, which afforded 0.15 g of the compound 441.

Production Example 62

First, 0.50 g of the compound 104 was dissolved in 30 ml of ethanol, to which a catalytic amount of p-toluenesulfonic acid was added, and the mixture was heated under reflux for 8 hours. After completion of the reaction, the reaction mixture was concentrated, and the residue thus obtained was subjected to silica gel chromatography (eluent; hexane:ethyl acetate=9:1), which afforded 0.15 g of the compound 250.

Production Example 63

First, 0.50 g of the compound 104 was dissolved in 30 ml of n-propanol, to which a catalytic amount of p-toluenesulfonic acid was added, and the mixture was heated under reflux for 8 hours. After completion of the reaction, the reaction mixture was concentrated, and the residue thus obtained was subjected to silica gel chromatography (eluent; hexane:ethyl acetate=9:1), which afforded 0.25 g of the compound 251.

Production Example 64

First, 0.50 g of the compound 104 was dissolved in 30 ml of iso-propanol, to which a catalytic amount of p-toluenesulfonic acid was added, and the mixture was heated under reflux for 8 hours. After completion of the reaction, the reaction mixture was concentrated, and the residue thus obtained was subjected to silica gel chromatography (eluent; hexane:ethyl acetate=9:1), which afforded 0.15 g of the compound 252.

Production Example 65

First, 0.50 g of the compound 104 was dissolved in 10 ml of benzyl alcohol, to which a catalytic amount of p-toluenesulfonic acid was added, and the mixture was heated under reflux for 8 hours. After completion of the reaction, the reaction mixture was subjected to silica gel chromatography (eluent; hexane:ethyl acetate=9:1), which afforded 0.30 g of the compound 253.

Production Example 66

First, 0.50 g of the compound 104 was dissolved in 30 ml of allyl alcohol, to which a catalytic amount of p-toluenesulfonic acid was added, and the mixture was heated under reflux for 8 hours. After completion of the reaction, the reaction mixture was concentrated, and the residue thus obtained was subjected to silica gel chromatography (eluent; hexane:ethyl acetate=9:1), which afforded 0.25 g of the compound 255.

Production Example 67

First, 0.50 g of the compound 104 was dissolved in 30 ml of 3-buten-1-ol, to which a catalytic amount of p-toluenesulfonic acid was added, and the mixture was heated under reflux for 8 hours. After completion of the reaction, the reaction mixture was concentrated, and the residue thus obtained was subjected to silica gel chromatography (eluent; hexane:ethyl acetate=9:1), which afforded 0.40 g of the compound 256.

Production Example 68

First, 0.50 g of the compound 104 was dissolved in 30 ml of 2-methoxyethanol, to which a catalytic amount of p-toluenesulfonic acid was added, and the mixture was heated under reflux for 8 hours. After completion of the reaction, the reaction mixture was concentrated, and the residue thus obtained was subjected to silica gel chromatography (eluent; hexane:ethyl acetate=9:1), which afforded 0.35 g of the compound 257.

Production Example 69

First, 0.50 g of the compound 104 was dissolved in 30 ml of cyclopentanol, to which a catalytic amount of p-toluenesulfonic acid was added, and the mixture was heated under reflux for 8 hours. After completion of the reaction, the reaction mixture was concentrated, and the residue thus obtained was subjected to silica gel chromatography (eluent; hexane:ethyl acetate=9:1), which afforded 0.40 g of the compound 258.

Production Example 70

First, 5.7 g of the compound 2-15 and 3.8 g of 1,1,1-trifluoro-3-bromoacetone were added to 100 ml of toluene, and the mixture was heated under reflux for 2 hours. After completion of the reaction, the reaction mixture was poured into water, to which saturated aqueous sodium bicarbonate solution was added, and the mixture was extracted with ethyl acetate. The organic layer was dried with magnesium sulfate and concentrated. The residue thus obtained was subjected to silica gel chromatography (eluent; hexane:ethyl acetate= 3:1), which afforded 6.3 g of the compound 116.

The melting point or $^1$H-NMR data for some of the compounds in Tables 1 to 5 are shown below.

Compound 101: m.p., 94.9° C.

Compound 102: $^1$H-NMR [CDCl$_3$, 60 MHz] δ(ppm): 2.15 (3H, s), 3.40 (3H, s), 3.64 (2H, s), 3.68 (3H, s), 5.51 (1H, s), 7.14 (1H, d, J=10 Hz), 7.24, 1H), d,J=8Hz)

Compound 103: m.p., 100.7° C.

Compound 104 $^1$H-NMR [CDCl$_3$, 60 MHz] δ(ppm): 3.50 (3H, s), 3.60 (2H, s), 3.67 (3H, s), 6.57 (1H, s), 7.18 (1H, d, J=11Hz), 7.20 (1H, d, J=9Hz)

Compound 105: $^1$H-NMR [CDCl$_3$, 60 MHz] δ(ppm): 1.38 (9H, s), 3.63 (3H, s), 3.68 (5H, s), 5.66 (1H, s), 7.16 (1H, d, J=10Hz), 7.23 (1H, d, J=8Hz)

Compound 106: $^1$H-NMR [CDCl$_3$, 60 MHz] δ(ppm): 1.32 (6H, d, J=6 Hz), 2.05 (3H, s), 3.39 (3H, s), 4.42 (1H, sp, J=6 Hz), 5.57 (1H, s), 6.77 (1H, d, J =8 Hz), 7.08 (1H, d, J=10 Hz)

Compound 107: $^1$H-NMR [CDCl$_3$, 60 MHz] δ(ppm): 1.31 (6H, d, J=6 Hz), 1.33 (9H, s), 3.58 (3H, s), 4.41 (1H, sp, J=6Hz), 5.60 (1H, s), 6.78 (1H, d, J =8 Hz), 7.11 (1H, d, J=10 Hz)

Compound 108: m.p., 60.9° C.

Compound 109: m.p., 119.4° C. (alecomp.)

Compound 110: $^1$H-NMR [CDCl$_3$, 60 MHz] δ(ppm): 1.25 (3H, t, J=7 Hz), 1.65 (3H, d, J=7 Hz), 3.52 (3H, s), 4.20 (2H, q, J=7 Hz), 4.63 (1H, t, J=7 Hz), 6.54 (1H, s), 6.62 (1H, d, J=8 Hz), 7.14 (1H, d, J=8 Hz)

Compound 111: m.p., 118.7° C.

Compound 112: m.p., 88.2° C.

Compound 113: $^1$H-NMR [CDCl$_3$,60 MHz] δ(ppm): 3.55 (3H, s), 4.56 (2H, d, J=5 Hz), 5.38–6.40 (3H, m), 6.56 (1H, s), 6.64 (1H, d, J=7 Hz), 7.16 (1H, d, J=10 Hz)

Compound 114: m.p., 85.6° C.

Compound 115: m.p., 91.5° C.

Compound 116: $^1$H-NMR [CDCl$_3$, 300 MHz] a(ppm): δ(3H, d, J=7.11 Hz), 3.55 (3H, s), 3.67 (3H, s), 3.85 (1H, q, J=7.11 Hz), 6.57 (1H, s), 7.23 (1H, d, J=9.99 Hz), 7.29 (1H, d, J=8.53 Hz)

Compound 117: m.p., 149.4° C.

Compound 118: $^1$H-NMR [CDCl$_3$, 300 MHz] δ(ppm): 3.55 (3H, s), 3.90 (3H, s), 6.57 (1H, s), 7.23 (1H, d, J=10 Hz), 7.67 (1H, d, J=8.7 Hz)

Compound 119: $^1$H-NMR [CDCl$_3$, 300 MHz] δ(ppm): 1.35 (3H, d, J=6.2 Hz), 1.37 (3H, d, J=6.2 Hz), 3.56 (3H, s), 4.78 (0.5H, hp, J=6.2 Hz), 5.25 (0.5H, hp, J=6.2 Hz), 6.58 (1H, s), 7.22 (1H, d, J=10.1 Hz), 7.59 (1H, d, J= 8.8 Hz)

Compound 122: $^1$H-NMR [CDCl$_3$, 60 MHz] δ(ppm): 3.57 (3H, s), 6.61 (1H, s), 7.25 (1H, d, J=10 Hz), 7.72 (1H, d, J=8 Hz)

Compound 142: m.p., 128.7° C.

Compound 146: $^1$H-NMR [CDCl$_3$, 60 MHz] δ(ppm): 1.23 (3H, t, J=7 Hz), 1.49 (3H, d, J=7 Hz), 3.49 (3H,s), 3.9–4.82 (4H, complex), 6.25 (1H, d, J=8 Hz), 6.49 (1H, s), 7.14 (1H, d, J=10 Hz)

Compound 147: m.p., 159.7° C.

Compound 149: m.p., 123.6° C.

Compound 150: m.p., 121.8° C.

Compound 191: m.p., 72.1° C.

Compound 192: $^1$H-NMR [CDCl$_3$, 60 MHz] δ(ppm): 3.00 (3H, s), 3.53 (3H, s), 6.51 (1H, s), 6.21 (1H, dd, J=3, 8 Hz), 7.00 (1H, d, J=3 Hz), 7.31 (1H, d, J=8 Hz), 7.49 (bs, 1H)

Compound 194: m.p., 141.4° C.

Compound 211: $^1$H-NMR [CDCl$_3$, 60 MHz] δ(ppm): 3.50 (3H, s), 3.62–4.03 (2H, br), 6.42 (1H, d, J=8 Hz), 6.49 (1H, s), 7.02 (1H, d, J=10 Hz)

Compound 212: m.p., 176.8° C.

Compound 213: m.p., 151.4° C.

Compound 214: m.p., 108.1° C.

Compound 223: $^1$H-NMR [CDCl$_3$, 300 MHz] δ(ppm): 1.39 (3H, t, J=7.1 Hz), 3.55 (3H, s), 4.37 (2H, q, J=7.1 Hz), 6.57 (1H, s), 7.22 (1H, d, J=10.1 Hz), 7.64 (1H, d, J=8.8 Hz)

Compound 228: m.p., 63.4° C.

Compound 229: m.p., 123.1 ° C.

Compound 232: $^1$H-NMR [CDCl$_3$, 60 MHz] δ(ppm): 2.28 (3H, s), 3.50 (3H, s), 3.75 (3H, s), 4.70 (2H, s), 6.54 (1H, s), 7.00 (1H, d, J=7 Hz), 7.18 (1H, d, J=9 Hz)

Compound 240: $^1$H-NMR [CDCl$_3$, 60 MHz] δ(ppm): 2.21 (3H, s), 3.51 (3H, s), 6.52 (1H, s), 7.02 (1H, dd, J=3.8 Hz), 7.22 (1H, d, J=3 Hz), 7.38 1H, d, J=8 Hz)

Compound 241: m.p., 116.2° C.

Compound243: $^1$H-NMR [CDCl$_3$, 60 MHz] δ(ppm): 2.17 (1.05H, s), 2.29 (1.95H, s), 3.49 (3H, s), 3.73 (3H, s), 4.53 (0.7H, s), 4.70 (1.3H, s), 6.50 (1H, s), 6.80–7.14 (2H, complex), 7.32 (1H, d, J=9 Hz)

Compound 247: m.p., 159.2° C.

Compound 250: $^1$H-NMR [CDCl$_3$, 300 MHz] δ(ppm): 1.23 (3H, t, J=7.15 Hz), 3.54 (3H, s), 3.62 (2H, s), 4.16 (2H, q, J=7.15 Hz), 6.57 (1H, s), 7.21 (1H, d, J=8.33 Hz), 7.21 (1H, d, J=9.96 Hz)

Compound 251: $^1$H-NMR [CDCl$_3$, 250 MHz] δ(ppm): 0.91 (3H, t, J=7.40 Hz), 1.57–1.71 (2H, m), 3.55 (3H, s), 3.65 (2H, s), 4.07 (2H, t, J=6.69 Hz), 6.58 (1H, s), 7.22 (1H, d, J=9.04 Hz), 7.22 (1H, d, J=9.04 Hz)

Compound 252: $^1$H-NMR [CDCl$_3$, 250 MHz] δ(ppm): 1.21 (6H, d, J=6.25 Hz), 3.54 (3H, s), 3.61 (2H, s), 5.00 (1H, qq, J=6.25 Hz), 6.58 (1H, s), 7.20 (1H, d, J=10.1 Hz), 7.21 (1H, d, J=8.18 Hz)

Compound 253: $^1$H-NMR [CDCl$_3$, 250 MHz] δ(ppm): 3.53 (3H, s), 3.67 (2H, s), 5.13 (2H, s), 6.52 (1H, s), 7.13–7.42 (7H, m)

Compound 255: $^1$H-NMR [CDCl$_3$, 300 MHz] δ(ppm): 3.54 (3H, s), 3.65 (2H, s), 4.59 (2H, d, J=4.81 Hz), 5.16–5.32 (2H, m), 5.79–5.99 (1H, m), 6.56 (1H, s), 7.20 (1H, d, J=9.95 Hz), 7.22 (1H, d, J=8.34 Hz)

Compound 256: $^1$H-NMR [CDCl$_3$, 300 MHz] δ(ppm): 2.35 (2H, td, J=6.78, 6.78 Hz), 3.54 (3H, s), 3.63 (2H, s), 4.15 (2H, t, J=6.78 Hz), 5.02–5.11 (2H, m), 5.66–5.79 (1H, m), 6.56 (1H, s), 7.20 (1H, d, J=8.7 Hz), 7.20 (1H, d, J=9.64 Hz)

Compound 257: ¹H-NMR [CDCl₃, 300 MHz] δ(ppm): 3.35 (3H, s), 3.54 (3H, s), 3.56 (2H, t, J=4.74 Hz), 3.67 (2H, s), 4.25 (2H, t, J=4.74 Hz), 6.57 (1H, s), 7.20 (1H, d, J=9.94 Hz), 7.22 (1H, d, J=8.34 Hz)

Compound 258: ¹H-NMR [CDCl₃, 300 MHz] δ(ppm): 1.53–1.82 (8H, m), 3.54 (3H, s), 3.59 (2H, s), 5.15–5.19 (1H, m), 6.57 (1H, s), 7.19 (1H, d, J= 8.87 Hz), 7.20 (1H, d, J=9.61 Hz)

Compound 301: m.p., 158.9° C.

Compound 302: ¹H-NMR [CDCl₃, 60 MHz] δ(ppm): 0.87 (3H, t, J=7 Hz), 1.55 (3H, d, J=7 Hz), 1.58–2.35 (2H, m), 3.57 (3H, s), 4.47 (1H, m), 6.57 (1H, s), 6.90 (1H, d, J=7 Hz), 7.17 (1H, d, J=10 Hz)

Compound 303: ¹H-NMR [CDCl₃, 60 MHz] δ(ppm): 0.86 (3H, t, J=7 Hz), 1.33 (9H, s), 1.50 (3H, d, J=7 Hz), 1.55–2.30 (2H, m), 3.63 (3H, s), 4.20–4.80 (1H, m), 5.64 (1H, s), 7.0 (1H, d, J=8 Hz), 7.14 (1H, d, J=10 Hz)

Compound 330: ¹H-NMR [CDCl₃, 60 MHz] δ(ppm): 0.87 (3H, t, J=7 Hz), 1.44–2.40 (complex, 5H), 3.57 (3H, s), 4.50 (1H, sextet, J=7 Hz), 6.55 (1H, s), 6.88 (1H, d, J=7 Hz), 7.12 (1H, d, J=10 Hz)

Compound 332: ¹H-NMR [CDCl₃, 60 MHz] δ(ppm): 0.89 (3H, t, J=7 Hz), 1.48–2.45 (complex, 5H), 3.66 (3H, s), 4.56 (1H, sextet, J=7 Hz), 6.58 (1H, s), 6.94 (1H, d, J=7 Hz), 7.20 (1H, d, J=10 Hz)

Compound 401: m.p., 179.2° C.

Compound 402: m.p., 119.5° C.

Compound 403: m.p., 148.7° C.

Compound 412: ¹H-NMR [CDCl₃, 250 MHz] δ(ppm): 3.56 (3H, s), 4.68 (2H, s), 4.79 (2H, s), 6.58 (1H, s), 6.76 (1H, d, J=7.42 Hz), 6.88 (1H, d, J=103 Hz)

Compound 416: ¹H-NMR [CDCl₃, 60 MHz] δ(ppm): 1.20 (3H, t, J=7 Hz), 1.62 (3H, d, J=7 Hz), 3.51 (3H, s), 4.18 (2H, q, J=7 Hz), 4.57 (2H, s), 5.27 (1H, q, J=7 Hz), 6.52 (1H, d, J=7 Hz), 6.58 (1H, s), 6.81 (1H, d, J=10 Hz)

Compound 424: ¹H-NMR [CDCl₃, 250 MHz] δ(ppm): 2.27 (1H, t, J=2.38 Hz), 3.53 (3H, s), 4.63 (2H, s), 4.66 (2H, d, J=2.38 Hz), 6.51 (1H, s), 6.71 (1H, dd, J=8.48, 2.34 Hz), 6.88 (1H, d, J=2.34 Hz), 6.89 (1H, d, J=8.48 Hz)

Compound 431: ¹H-NMR [CDCl₃, 60 MHz] δ(ppm): 0.59–2.09 (9H, complex), 1.62 (3H, d, J=7 Hz), 3.54 (3H, s), 4.12 (2H, t, J=8 Hz), 4.59 (2H, s), 5.34 (1H, q, J=7 Hz), 6.52 (1H, d, J=7 Hz), 6.59 (1H, s), 6.72 (1H, d, J=11Hz)

Compound 434: ¹H-NMR [CDCl₃, 60 MHz] δ(ppm): 2.27 (1H, t, J=2 Hz), 3.56 (3H, s), 4.59 (4H, s), 6.50 (1H, s), 6.77 (1H, d, J=10 Hz), 6.85 (1H, d, J =7 Hz)

Compound 437: ¹H-NMR [CDCl₃, 250 MHz] δ(ppm): 2.28 (1H, t, J=2.43 Hz), 3.40 (3H, s), 4.64 (2H, s), 4.66 (2H, d, J=2.43 Hz), 5.86 (1H, s), 6.83 (1H, d, J=10.5 Hz), 7.01 (1H, d, J=7.78 Hz), 7.37–7.48 (5H, m)

Compound 438: ¹H-NMR [CDCl₃, 300 MHz] δ(ppm): 1.37 (3H, t, J=7.16 Hz), 2.25 (1H, t, J=2.51 Hz), 3.77 (3H, s), 4.33 (2H, q, J=7.16 Hz), 4.63 (2H, s), 4.64 (2H, d, J=2.51 Hz), 6.81 (1H, d, J=10.4 Hz), 6.90 (1H, d, J= 7.75 Hz), 7.00 (1H,s)

Compound 439: ¹H-NMR [DMSO-d₆, 250 MHz] δ(ppm): 3.27 (1H, t, J=2.36 Hz), 3.63 (3H, s), 4.71 (4H, s), 6.95 (1H, d, J=8.08 Hz), 7.05 (1H, d, J=10.9 Hz), 7.27 (1H, s)

Compound 441: ¹H-NMR [CDCl₃, 250 MHz] δ(ppm): 2.27 (1H, t, J=2.42 Hz), 3.58 (3H, s), 4.64 (4H, s), 6.83 (1H, d, J=11.57 Hz), 6.87 (1H, d, J=7.64 Hz), 7.26 (1H, s)

Compound 501: ¹H-NMR [CDCl₃, 60 MHz] δ(ppm): 2.41 (3H, s), 3.53 (3H, s), 6.38 (1H, s), 6.53 (1H, s), 7.02 (1H, d, J=11 Hz)

Compound 609: ¹H-NMR [CDCl₃, 60 MHz] δ(ppm): 1.85 (3H, s), 3.55 (3H, s), 3.50–4.00 (4H, m), 6.50 (1H, s), 7.00 (1H, d, J=10 Hz)

The production examples of the starting compounds for the present compound will be described as the following reference examples.

Reference Example 1

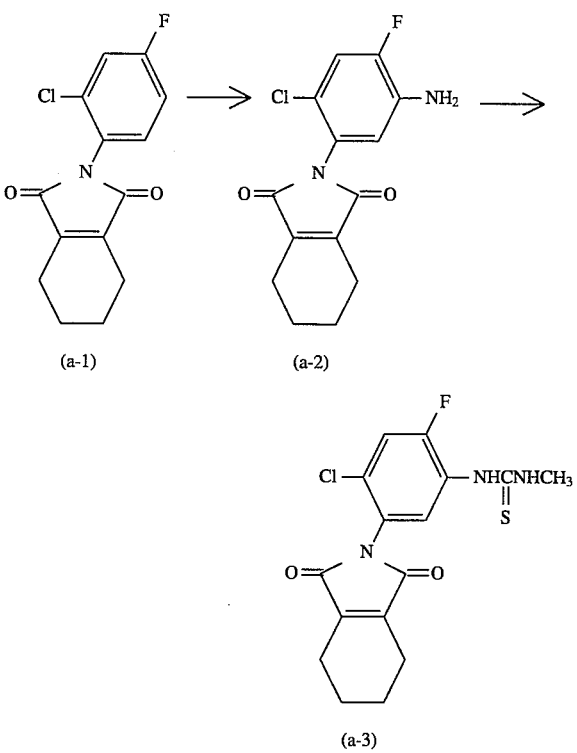

First, 38 g of the compound a-1 obtained by the process as described in Japanese Patent Laid-open Publication No. 54-19965 was dissolved in 250 ml of sulfuric acid, to which 9.0 g of fuming nitric acid was added dropwise while ice cooling. After 2 hours, the reaction mixture was poured into ice water, which was then extracted with ethyl acetate. The organic layer was washed with water, neutralized with potassium carbonate, and dried with magnesium sulfate, followed by hydrogenation with 5% Pd-C catalyst. After completion of the reaction, the catalyst was removed by filtration, and the organic layer was concentrated. The residue thus obtained was subjected to silica gel chromatography (eluent; hexane: ethyl acetate=2:1), which afforded 31 g of the compound a-2.

Then, 20 g of the compound a-2 was dissolved in 300 ml of toluene, to which 9.3 g of thiophosgene was added, and the mixture was heated under reflux for 2 hours, followed by removal of toluene by evaporation. The residue thus obtained was dissolved in 200 ml of chloroform, to which 8.0 g of methylamine (40% methanol solution) was added, and the mixture was stirred at room temperature for 2 hours. After completion of the reaction, the reaction mixture was poured into water, which was then neutralized with diluted hydrochloric acid, washed with water, dried with magnesium sulfate, and concentrated. The residue thus obtained was subjected to silica gel chromatography (eluent; hexane: ethyl acetate=2:1), which afforded 19 g of the compound a-3.

Reference Example 2

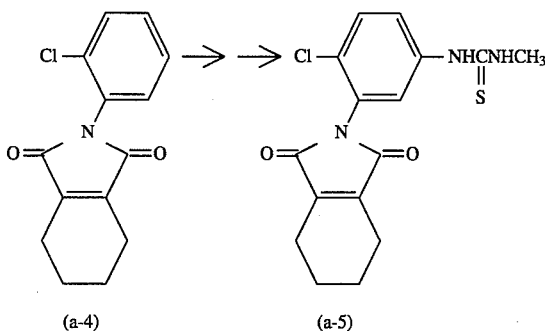

(a-4)     (a-5)

The compound a-5 can be derived from the compound a-4 by the process according to Reference Example 1.

The following will describe formulation examples. The present compounds are designated by the corresponding compound numbers as shown in Tables 1 to 5. In these formulation examples, parts are all by weight.

Formulation Example 1

Fifty parts of each of the compounds 101-261, 301-338, 401-441, 501-523 and 601-628, 3 parts of calcium ligninsulfonate, 2 parts of sodium laurylsulfate and 45 parts of synthetic hydrous silicate are well pulverized and mixed to give a wettable powder for each compound.

Formulation Example 2

Ten parts of each of the compounds 101-261, 301-338, 401-441, 501-523 and 601-628, 14 parts of polyoxyethylene styryl phenyl ether, 6 parts of calcium dodecylbenzenesulfonate, 35 parts of xylene and 35 parts of cyclohexanone are well mixed to give an emulsifiable concentrate for each compound.

Formulation Example 3

Two parts of each of the compounds 101-261, 301-338, 401-441, 501-523 and 601-628, 2 pans of synthetic hydrous silicate, 2 parts of calcium ligninsulfonate, parts of bentonite and 64 parts of kaoline clay are well pulverized and mixed, to which water is added, and the mixture is well kneaded, granulated and dried to give a granule for each compound.

Formulation Example 4

Twenty five parts of each of the compounds 101, 103, 301 and 401-403, 50 pans of 10% aqueous solution of polyvinyl alcohol and 25 parts of water are well mixed, and the mixture was then pulverized until the mean particle size becomes not greater than 5 μm to give a flowable for each compound.

The following test examples will demonstrate that the present compounds are useful as an active ingredient of herbicides. The present compounds are designated by the corresponding compound numbers as shown in Tables 1 to 5.

The herbicidal activity and the phytotoxicity to crop plants were evaluated at 6 levels with indices of 0 to 5, wherein "0" means that there was no or little difference in the degree of germnation or growth between the test plants and the untreated plants, and "5" means that the test plants died complete or their germination or growth was completely inhibited. The herbicidal activity is excellent when rated at "5" or "4" but insufficient when rated at "3", "2", "1" or "0". The phytotoxicity to crop plants has no problem on practical use when rated at "0" or "1" but unacceptable when rated at "2", "3", "4" or "5".

Test Example 1: Soil surface treatment on upland field

Cylindrical plastic pots of 10 cm in diameter and 10 cm in depth were filled with soil, and the seeds of velvetleaf (*Abutilon theophrasti*) were sowed in the soil. Each of the test compounds 104, 150, 402 and 434 was formulated into an emulsifiable concentrate according to Formulation Example 2, which was then diluted with water. The dilution was unifom-dy sprayed over the soil surface in the pots with a sprayer at a volume of 1000 liters per hectare. For this treatment, each of the test compounds was applied at an amount of 500 grams per hectare. After the spraying, the test plants were grown in a greenhouse for 19 days, and the herbicidal activity was examined.

As a result, it was found that all the test compounds exhibited the highest herbicidal activity "5" to velvetleaf.

Test Example 2: Foliar treatment on upland field

Cylindrical plastic pots of 10 cm in diameter and 10 cm in depth were filled with soil, and the seeds of velvetleaf (*Abutilon theophrasti*) were sowed in the soil. After growing in a greenhouse, the plants at the cotyledon to 1.5 leaf stage were prepared. Then, each of the test compounds 101, 103–106, 108, 117–119, 146, 147, 149, 150, 223, 228, 232, 241, 243, 260, 302, 330, 332, 402, 403, 412, 416, 431, 434, 438, 439, 440, 441 and 609 was formulated into an emulsifiable concentrate according to Formulation Example 2, which was then diluted with water containing a spreading agent. The dilution was uniformly sprayed over the foliage of the test plants with a sprayer at a volume of 1000 liters per hectare. For this treatment, each of the test compounds was applied at an amount of 500 grams per hectare. After the spraying, the test plants treated with any other compound than the compounds 441 and 609 were grown in the greenhouse for 19 days and the test plants treated with the compound 441 or 609 were grown in the greenhouse for 16 days, and the herbicidal activity was examined.

As a result, it was found that all the test compounds exhibited the highest herbicidal activity "5" to velvetleaf.

Test Example 3: Flooding treatment on paddy field

Cylindrical plastic pots of 9 cm in diameter and 11 cm in depth were filled with soil, and the seeds of barnyardgrass (*Echinochloa oryzicola*) were sowed in the soil. These pots were then flooded to form a paddy field. After growing in a greenhouse, the plants at the 0.8 to 1.0 leaf stage were prepared. Then, each of the test compounds 103, 104, 108, 110–116, 118, 119, 146, 149, 150, 223, 232, 252, 261, 302, 330, 332, 401, 402, 412, 416, 424, 425, 431, 434, 441, 501 and 609 was formulated into an emulsifiable concentrate according to Formulation Example 2, which was then diluted with water. The dilution was applied to the water surface in the pots with a syringe at a volume of 5000 liters per hectare. For this treatment, each of the test compounds was applied at an amount of 250 grams per hectare. After the application, the test plants treated with any other compound than the compounds 441 and 609 were grown in the greenhouse for 19 days and the test plants treated with the compound 441 or 609 were grown in the greenhouse for 22 or 16 days, respectively, and the herbicidal activity was examined.

As a result, it was found that all the test compounds exhibited the highest herbicidal activity "5" to barnyardgrass.

Test Example 4: Soil treatment on upland field

Box-type plastic pots of 32×22 cm² in bottom area and 8 cm in depth were filled with soil, and the seeds of pale smartweed (*Polygonum lapathifolium*), velvetleaf (*Abutilon theophrasti*), giant foxtail (*Setaria faberi*) and corn (*Zea mays*) were sowed in the soil. Each of the test compounds 103, 119 and 302 was formulated into an emulsifiable concentrate according to Formulation Example 2, which was then diluted with water. The dilution was uniformly sprayed over the soil surface in the pots with a sprayer at a volume of 1050 liters per hectare. For this treatment, each of the test compounds was applied at an amount of 500 grams per hectare. After the spraying, the test plants were grown in a greenhouse for 25 days, and the herbicidal activity to pale smartweed, velvetleaf and giant foxtail, and the phytotoxicity to corn were examined.

As a result, it was found that all the test compounds exhibited the highest herbicidal activity "5" to pale smartweed, velvetleaf and giant foxtail, and the lowest phytotoxicity "0" to corn.

Test Example 5: Foliar treatment on upland field

Box-type plastic pots of 27×19 cm² in bottom area and 7 cm in depth were filled with soil, and the seeds of ivyleaf morningglory (*Ipomoea hederacea*) and common cocklebur (*Xanthium pensylvanicum*) were sowed in the soil. After growing in a greenhouse, the plants at the 1.2 to 5 leaf stage were prepared. Each of the test compounds 104, 110, 111, 114–116, 146, 223, 250–253,255–258, 302, 402 and 425 was formulated into an emulsifiable concentrate according to Formulation Example 2, which was then diluted with water. The dilution was uniformly sprayed over the foliage of the test plants in the pots with a sprayer at a volume of 1050 liters per hectare. For this treatment, each of the test compounds was applied at an amount of 250 grams per hectare. After the spraying, the test plants were grown in a greenhouse for 22 days, and the herbicidal activity was examined.

As a result, it was found that all the test compounds exhibited the highest herbicidal activity "5" to ivyleaf morningglory and common cocklebur.

Test Example 6: Foliar treatment on upland field

Box-type plastic pots of 17×12 cm² in bottom area and 7 cm in depth were filled with soil, and the seeds of catchweed bedstraw (*Galium aparine*) and sugar beet (*Beta vulgaris*) were sowed in the soil. After growing in a greenhouse, the plants at the 1.5 to 4 leaf stage were prepared. Then, each of the test compounds 232, 260 and 434 was formulated into an emulsifiable concentrate according to Formulation Example 2, which was then diluted with water. The dilution was uniformly sprayed over the foliage of the test plants in the pots with a sprayer at a volume of 1050 liters per hectare. For this treatment, the compound 260 was applied at an amount of 250 grams per hectare and the compounds 232 and 434 were applied respectively at an amount of 63 grams per hectare. After the spraying, the test plants treated with the compound 232 or 260 were grown in the greenhouse for 22 days and the test plants treated with the compound 434 were grown in the greenhouse for 21 days, and the herbicidal activity to catchweed bedstraw and the phytotoxicity to sugar beet were examined.

As a result, it was found that all the test compounds exhibited the highest herbicidal activity "5" to catchweed bedstraw and the lowest phytotoxicity "0" to sugar beet.

Test Example 7: Foliar treatment on upland field

Box-type plastic pots of 17×12 cm² in bottom area and 7 cm in depth were filled with soil, and the seeds of catchweed bedstraw (*Galium aparine*) and wheat (*Triticum aestivum*) were sowed in the soil. After growing in a greenhouse, the plants at the 1.5 to 2.5 leaf stage were prepared. Then, each of the test compounds 332, 434 and 501 was formulated into an emulsifiable concentrate according to Formulation Example 2, which was then diluted with water. The dilution was uniformly sprayed over the foliage of the test plants in the pots with a sprayer at a volume of 1050 liters per hectare. For this treatment, the compound 501 was applied at an amount of 125 grams per hectare and the compounds 332 and 434 were applied respectively at an amount of 63 grams per hectare. After the spraying, the test plants were grown in the greenhouse for 21 days, and the herbicidal activity to catchweed bedstraw and the phytotoxicity to wheat were examined.

As a result, it was found that all the test compounds exhibited the highest herbicidal activity "5" to catchweed bedstraw and the lowest phytotoxicity "0" to wheat.

Test Example 8: Flooding treatment on paddy field

Cylindrical plastic pots of 9 cm in diameter and 11 cm in depth were filled with soil, and the seeds of barnyardgrass (*Echinochloa oryzicola*) were sowed in the soil, to which rice seedlings were transplanted. These pots were then flooded to form a paddy field. After growing in a greenhouse, the plants at the 2 to 3.1 leaf stage were prepared. Then, each of the test compounds 103, 223 and 412 was formulated into an emulsifiable concentrate according to Formulation Example 2, which was then diluted with water. The dilution was applied to the water surface in the pots with a syringe at a volume of 5000 liters per hectare. For this treatment, each of the test compounds was applied at an amount of 250 grams per hectare. After the application, the test plants treated with the compound 103, 223 or 412 were grown in the greenhouse for 20, 24 or 21 days, respectively, and the herbicidal activity to barnyardgrass and the phytotoxicity to rice was examined.

As a result, it was found that all the test compounds exhibited the highest herbicidal activity "5" to barnyardgrass and the lowest phytotoxicity "0" to rice.

Test Example 9: Soil treatment on upland field

Box-type plastic pots of 32×22 cm² in bottom area and 8 cm in depth were filled with soil, and the seeds of redroot pigweed (Amaranth. vs retrofiexus), common lambsquarters (*Chenopodium album*), black nightshade (*Solanum nigrum*), large crabgrass (*Digitaria sanguinalis*) and soybean (*Glycine max*) were sowed in the soil. Each of the test compounds 115 and 402 was formulated into an emulsifiable concentrate according to Formulation Example 2, which was then diluted with water. The dilution was uniformly sprayed over the soil surface in the pots with a sprayer at a volume of 775 liters per hectare. For this treatment, each of the test compounds was applied at an amount of 300 grams per hectare. After the spraying, the test plants were grown in a greenhouse for 28 days, and the herbicidal activity to redroot pigweed, common lamb-squarters, black nightshade and large crabgrass, and the phytotoxicity to soybean were examined.

As a result, it was found that all the test compounds exhibited the highest herbicidal activity "5" to redroot pigweed, common lambsquarters, black nightshade and large crabgrass, and the lowest phytotoxicity "0" to soybean.

Test Example 10: Foliar treatment on upland field

Cylindrical plastic pots of 24 cm in diameter and 21 cm in depth were filled with soil, and the seeds of ivyleaf morningglory (*Ipomoea hederacea*), tall morningglory (*Ipomoea purpurea*), velvetleaf (*Abutilon theophrasti*), soybean (*Glycine max*) and corn (*Zea mays*) were sowed in the soil. After growing outdoors, the plants at the 2 to 4 leaf stage were prepared. Then, each of the test compounds 104, 253 and 255 was formulated into an emulsifiable concentrate according to Formulation Example 2, which was then diluted with water containing a spreading agent. The dilution was uniformly sprayed over the foliage of the test plants with a sprayer at a volume of 600 liters per hectare. Also 23% emulsifiable concentrate (commercially available formulation) of fomesafen (trade name: Reflex) as a reference compound was diluted with water containing a spreading agent, and the dilution was uniformly sprayed over the foliage of the test plants with a sprayer at a volume of 600 liters per hectare. For this treatment, each of the test compounds including the reference compound was applied at an amount of 100 grams per hectare. After the spraying, the test plants were grown outdoors for 32 days, and the herbicidal activity to ivyleaf morningglory, tall morningglory and velvetleaf, and the phytotoxicity to soybean and corn were examined.

As a result, it was found that all the test compounds exhibited the highest herbicidal activity "5" to ivyleaf morningglory, tall morningglory and velvetleaf, and the lowest phytotoxicity "0" to soybean and corn: on the other hand, the reference compound, fomesafen, exhibited the lowest phytotoxicity "0" to soybean and corn but insufficient herbicidal activity "3" to ivyleaf morningglory and "2" to tall morningglory and velvetleaf.

What is claimed is:

1. An iminothiazoline compound of the general formula:

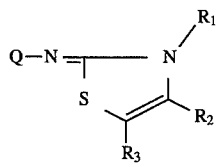

[1]

wherein $R_1$ is $C_1$–$C_6$ (halo)alkyl, $C_3$–$C_6$ (halo)alkenyl, $C_3$–$C_6$ (halo) alkynyl, $C_3$–$C_7$ (halo) cycloalkyl, $C_3$–$C_7$ cycloalkyl $C_1$–$C_3$ $R_2$ is $C_1$–$C_6$ alkyl substituted with one or more halogen atoms; cyano or a group of the general formula: $CO_2R_7$ or $CONR_8R_9$;

$R_3$ is hydrogen, $C_1$–$C_6$ (halo)alkyl or a group of the general formula: $CO_2R_6$;

Q is a group of the general formula:

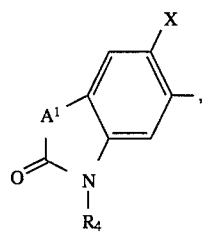

(Q-1)

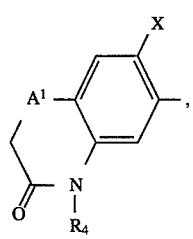

(Q-2)

-continued

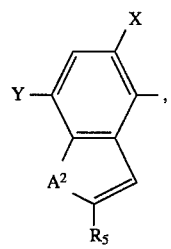

(Q-3)

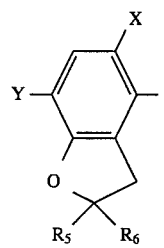

(Q-4)

or

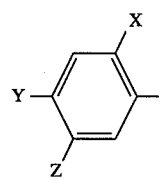

(Q-5)

X is hydrogen, chlorine or fluorine;

Y is chlorine, fluorine, bromine, nitro or cyano;

$A^1$ is oxygen, sulfur, —$CH_2$ or —NH;

$A^2$ is oxygen or sulfur;

$R_4$ is $_1$–$C_6$ (halo)alkyl, $C_3$–$C_6$ (halo)alkenyl, $C_3$–$C_6$ (halo) alkynyl, $C_3$–$C_7$ (halo)cycloalkyl, cyano $C_1$–$C_3$ alkyl, $C_1$–$C_3$ (halo) alkoxy $C_1$–$C_3$ (halo) alkyl, ($C_1$–$C_6$ (halo) alkyl) carbonyl, ($C_1$–$C_6$ alkoxy) carbonyl, hydrogen or a group of the general formula:

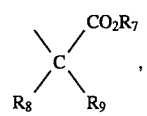

(P-1)

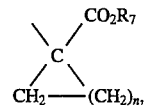

(P-2)

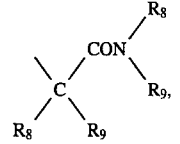

(P-3)

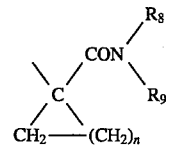

(P-4)

or

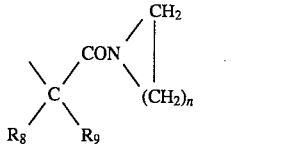
(P-5)

$R_5$ is hydrogen, $C_1$–$C_6$ (halo)alkyl or a group of the general formula: $CH_2OR_4$ or $CO_2R_7$;

$R_6$ is hydrogen or $C_1$–$C_3$ (halo) alkyl;

Z is nitro, cyano, $SO_2Cl$, tetrahydrophthalimide or a group of the general formula: $CO_2R_7$, $CR_6$=$NOR_4$, $CH$=$C(R_6)CO_2R_7$, $CHX^1CHX^2CO_2R_7$, $SR_4$, $OR_4$, $NHR_4$, $NHSO_2R_{10}$, $COR_6$ or $SO_2OR_4$;

$X^1$ and $X^2$ are the same or different and are independently hydrogen, chlorine or bromine;

$R_7$ is hydrogen, $C_1$–$C_{10}$ (halo) alkyl, $C_3$–$C_7$ (halo)cycloalkyl, $C_3$–$C_7$ cycloalkenyl, $C_3$–$C_6$ (halo) alkenyl, $C_3$–$C_6$ (halo) alkynyl, cyano $C_1$–$C_3$ alkyl, $C_1$–$C_3$ alkoxy $C_1$–$C_3$ alkyl, ($C_1$–$C_5$ (halo)alkoxy)carbonyl $C_1$–$C_3$ alkyl, aryl which may be substituted with one or more $C_1$–$C_3$ (halo)alkyl groups, $C_1$–$C_3$ (halo)alkoxy groups or halogen atoms, benzyl or a group of the general formula: N=$CR_6R_6$, $NR_6R_6$ or

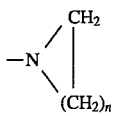

$R_8$ and $R_9$ are the same or different and are independently hydrogen, $C_1$–$C_6$ (halo) alkyl, $C_3$–$C_6$ (halo) alkenyl or $C_3$–$C_6$ (halo) alkynyl;

$R_{10}$ is $C_1$–$C_6$ (halo)alkyl, $C_3$–$C_8$ (halo)cycloalkyl or aryl which may be substituted with one or more $C_1$–$C_3$ (halo) alkyl groups, $C_1$–$C_3$ (halo) alkoxy groups or halogen atoms;

n is an integer of 1 to 5; and the term "(halo)" as used in the names of the above substituents means that they may be substituted with one or more halogen atoms.

2. The iminothiazoline compound according to claim 1, wherein $R_2$ is $C_1$–$C_3$ alkyl substituted with one or more halogen atoms.

3. The iminothiazoline compound according to claim 1, wherein $R_2$ is trifluoromethyl, chlorodifluoromethyl, difluoromethyl or pentafluoroethyl.

4. The iminothiazoline compound according to claim 1, wherein $R_2$ is trifluoromethyl.

5. The iminothiazoline compound according to claim 1, wherein $R_1$ is $C_1$–$C_6$ (halo)alkyl.

6. The iminothiazoline compound according to claim 1, wherein $R_1$ is $C_1$–$C_3$ alkyl.

7. The iminothiazoline compound according to claim 1, wherein $R_1$ is methyl.

8. The iminothiazoline compound according to claim 1, wherein $R_3$ is hydrogen or a group of the general formula: $CO_2R_6$.

9. The iminothiazoline compound according to claim 1, wherein $R_3$ is hydrogen.

10. The iminothiazoline compound according to claim 1, wherein Q is (Q-1), (Q-2) or (Q-5).

11. The iminothiazoline compound according to claim 1, wherein $R_1$ is methyl, $R_2$ is trifluoromethyl, $R_3$ is hydrogen, Q is (Q-5), X is fluorine, Y is chlorine, and Z is $SCH_2COOCH_3$.

12. The iminothiazoline compound according to claim 1, wherein $R_1$ is methyl, $R_2$ is chlorodifluoromethyl, $R_3$ is hydrogen, Q is (Q-1), X is fluorine, $A^1$ is sulfur and $R_4$ is sec-butyl.

13. The iminothiazoline compound according to claim 1, wherein $R_1$ is methyl, $R_2$ is trifluoromethyl, $R_3$ is hydrogen, Q is (Q-2), X is fluorine, $A^1$ is oxygen, and $R_4$ is propargyl.

14. A herbicide comprising a herbicidally effective amount of an iminothiazoline compound according to claim 1.

15. A method for controlling unfavorable weeds, which comprises applying a herbicidally effective amount of an iminothiazoline compound according to claim 1 to an area where the unfavorable weeds grow or will grow.

16. The iminothiazoline compound according to claim 1, wherein Q is (Q-1).

17. The iminothiazoline compound according to claim 1, wherein Q is (Q-2).

18. The iminothiazoline compound according to claim 1, wherein Q is (Q-3).

19. The iminothiazoline compound according to claim 1, wherein Q is (Q-4).

20. The iminothiazoline compound according to claim 1, wherein Q is (Q-5).

21. The iminothiazoline compound according to claim 20, wherein Z is nitro, cyano, $SO_2Cl_2$, tetrahydrophthalimide or a group of the general formula: $CO_2R_7$, $CR_6$=$NOR_4$, CH=C ($R_6$) $CO_2R_7$, $CHX^1CHX^2CO_2R_7$, $SR_4$, $NHR_4$, $NHSO_2$ -$R_{10}$, $COR_6$ or $SO_2OR_4$.

22. The iminothiazoline compound according to claim 20, wherein Z is $OR_4$, and $R_4$ is $C_3$–$C_6$ (halo) alkenyl, $C_3$–$C_6$ (halo)alkynyl, $C_3$–$C_7$ (halo)cycloalkyl, cyano $C_1$–$C_3$ alkyl, $C_1$–$C_3$ (halo) alkoxy $C_1$–$C_3$ (halo) alkyl, ($C_1$–$C_6$ (halo) alkyl) carbonyl, ($C_1$–$C_6$ alkoxy) carbonyl, hydrogen or a group of the general formula:

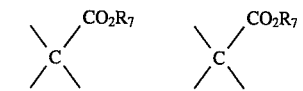 , 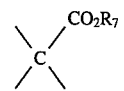 , (P-1)  (P-2)

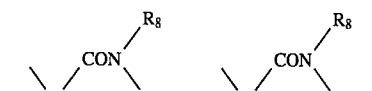 , 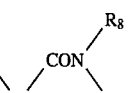 or (P-3)  (P-4)

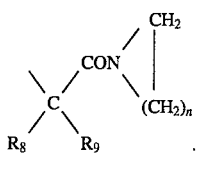

(P-5)

\* \* \* \* \*

UNITED STATES PATENT AND TRADEMARK OFFICE
CERTIFICATE OF CORRECTION

PATENT NO. :   5,521,145
DATED      :   May 28, 1996
INVENTOR(S) :  Takano et al.

It is certified that error appears in the above-indentified patent and that said Letters Patent is hereby corrected as shown below:

Column 1

Line 27, (line 1 below formula [1]), change "$C_1 14\ C_6$" to --$C_1$-$C_6$--

Line 36, change "forrnyl" to --formyl--

Column 49

Line 42, change "(alecomp.)" to --(decomp.)--

Column 57

Line 39 (line 1 below formula [1]), change "$C_1 C_6$" to --$C_1$-$C_6$--

Line 41, after "$C_1$-$C_3$" insert -- alkyl, cyano $C_1$-$C_3$ alkyl or $C_1$-$C_5$(halo) -alkyoxy $C_1$-$C_5$(halo)alkyl --

UNITED STATES PATENT AND TRADEMARK OFFICE
CERTIFICATE OF CORRECTION

PATENT NO. : 5,521,145
DATED : May 28, 1996
INVENTOR(S) : Takano, et al.

It is certified that error appears in the above-indentified patent and that said Letters Patent is hereby corrected as shown below:

Column 58

Line 36, change "$_1$-C$_6$" to --$C_1$-$C_6$--

Signed and Sealed this

Third Day of December, 1996

Attest:

BRUCE LEHMAN

Attesting Officer

Commissioner of Patents and Trademarks